US008557313B2

(12) United States Patent
Haaber et al.

(10) Patent No.: US 8,557,313 B2
(45) Date of Patent: *Oct. 15, 2013

(54) PHAGE RESISTANCE

(75) Inventors: Jakob Brandt Borup Haaber, Copenhagen (DK); Sylvain Moineau, Québec (CA); Karin Hammer, Rungsted Kyst (DK)

(73) Assignee: Danmarks Tekniske Universitet, Lyngby (DK)

( * ) Notice: Subject to any disclaimer, the term of this patent is extended or adjusted under 35 U.S.C. 154(b) by 657 days.

This patent is subject to a terminal disclaimer.

(21) Appl. No.: 12/665,855

(22) PCT Filed: Jul. 2, 2008

(86) PCT No.: PCT/DK2008/050166
§ 371 (c)(1),
(2), (4) Date: Apr. 21, 2010

(87) PCT Pub. No.: WO2009/003491
PCT Pub. Date: Jan. 8, 2009

(65) Prior Publication Data
US 2010/0209555 A1    Aug. 19, 2010

Related U.S. Application Data

(60) Provisional application No. 60/947,759, filed on Jul. 3, 2007.

(30) Foreign Application Priority Data

Jul. 3, 2007  (EP) .................................... 07111640

(51) Int. Cl.
*A23C 9/12*      (2006.01)
*C12N 1/20*      (2006.01)
(52) U.S. Cl.
USPC ................. 426/43; 426/34; 426/42; 426/580; 435/252.3; 435/320.1
(58) Field of Classification Search
USPC ......... 426/34, 42, 43, 49, 51, 52, 55, 53, 580; 435/252.3, 253.4, 320.1
See application file for complete search history.

(56) References Cited

U.S. PATENT DOCUMENTS

| | | | | |
|---|---|---|---|---|
| 5,580,787 A | * | 12/1996 | Wessels et al. | 435/320.1 |
| 5,618,723 A | * | 4/1997 | Klaenhammer et al. | 435/252.3 |
| 5,629,182 A | * | 5/1997 | Chopin et al. | 435/476 |
| 5,814,499 A | * | 9/1998 | Moineau et al. | 435/476 |
| 5,824,523 A | * | 10/1998 | Moineau et al. | 435/478 |
| 5,925,388 A | * | 7/1999 | Moineau et al. | 426/43 |
| 5,928,688 A | * | 7/1999 | Moineau et al. | 426/43 |
| 2004/0157312 A1 | * | 8/2004 | Moineau et al. | 435/252.3 |

FOREIGN PATENT DOCUMENTS

| | | |
|---|---|---|
| WO | WO 97/20917 A2 | 6/1997 |
| WO | WO 01/16329 A2 | 3/2001 |
| WO | WO 02/081697 A1 | 10/2002 |
| WO | WO 2004/020598 A2 | 3/2004 |
| WO | WO 2006/072631 A1 | 7/2006 |

OTHER PUBLICATIONS

Altschul, Stephen F. et al., "Gapped BLAST and PSI-BLAST: a new generation of protein database search programs" Nucleic Acids Research, 1997, pp. 3389-3402, vol. 25, No. 17.
Behnke, Detlev et al., "Bacteriophage interference in *Streptococcus pyogenes*—Characterization of prophage-host systems interfering with the virulent phage A25"Virology, 1978, pp. 118-128, vol. 85.
Bolotin, Alexander et al., "The complete genome sequence of the lactic acid bacterium *Lactococcus lactis* ssp. lactis IL1403" Genome Research, 2001, pp. 731-753, vol. 11.
Candry, P.S. et al., "Putative uncharacterized protein" Database UniProt, Jan. 1, 1998, XP-002465577.
Chandry, P. Scott et al., "Temporal transcription map of the *Lactococcus lactis* bacteriophage sk1" Microbiology, 1994, pp. 2251-2261, vol. 140.
Chandry, P. Scott et al., " Analysis of the DNA sequence, gene expression, origin of replication and modulator structure of the *Lactococcus lactis* lytic bacteriophage ski" Molecular Microbiology, 1997, pp. 49-64, vol. 26.
Chopin, Marie-Christine et al., "Phage abortive infection in lactococci: variations on a theme" Current Opinion in Microbiology, 2005, pp. 473-479, vol. 8.
Cluzel, Pierre-Jean et al., "Phage abortive infection mechanism from *Lactococcus lactis* subsp. lactis, expression of which is mediated by an Iso-ISS1 element" Applied and Environmental Microbiology, Dec. 1991, pp. 3547-3551, vol. 57, No. 12.
Coq, Anne-Marie Crutz-Le et al., "Sequence analysis of the *lactococcal* bacteriophage bIL170: insights into structural proteins and HNH endonucleases in dairy phages" Microbiology, 2002, pp. 985-1001, vol. 148.
Crutz-Le Coq, A.M. et al., "E24" Database UniProt, Nov. 1, 1998, XP-002465580.
Dupont, Kitt et al., "Identification of *Lactococcus lactis* genes required for bacteriophage adsorption" Applied and Environmental Microbiology, Oct. 2004, pp. 5825-5832, vol. 70, No. 10.
Emond, Eric et al., "Phenotypic and genetic characterization of bacteriophage abortive infection mechanism AbiK from *Lactococcus lactis*" Applied and Environmental Microbiology, Apr. 1997, pp. 1274-1283, vol. 63, No. 4.
Hayes, Finbarr et al., "Identification of the Minimal Replicon of *Lactococcus lactis* subsp. lactis UC317 Plasmid pC1305" Applied and Environmental Microbiology, Jan. 1990, pp. 202-209, vol. 56, No. 1.
Hill, Colin et al., "Rapid Method to Characterize Lactococcal Bacteriophage Genomes" Applied and Environmental Microbiology, Jan. 1991, pp. 283-288, vol. 57, No. 1.
Leenhouts, K. et al., "A general system for generating unlabelled gene replacements in bacterial chromosomes" Mol Gen Genet, 1996, pp. 217-224, vol. 253.

(Continued)

*Primary Examiner* — Leslie Wong
(74) *Attorney, Agent, or Firm* — Knobbe Martens Olson & Bear LLP

(57) ABSTRACT

The present invention relates to the field of dairy science. In particular, the present invention relates to methods for improving dairy starter culture quality as well as food products that can be obtained using such methods.

26 Claims, 6 Drawing Sheets

(56) References Cited

OTHER PUBLICATIONS

Lubbers, Mark W. et al., "Sequencing and analysis of the Prolate-headed *Lactococcal* bacteriophage c2 genome and identification of the structural genes" Applied and Environmental Microbiology, Dec. 1995, pp. 4348-4356, vol. 61, No. 12.

Lubbers, Mark W. et al., "Sequencing and analysis of the cos region of the *Lactococcal* bacteriophage c2" Mol Gen Genet, 1994, pp. 160-166, vol. 245.

Maguin, Emmanuelle et al., "Efficient insertional mutagenesis in *Lactococci* and other gram-positive bacteria" Journal of Bacteriology, Feb. 1996, pp. 931-935, vol. 178, No. 3.

Mahony, Jennifer et al., "Sequence and comparative genomic analysis of *Lactococcal* bacteriophages jj50, 712 and P008: evolutionary insights into the 936 phage species" FEMS Microbiol Lett, 2006, pp. 253-261, vol. 261.

Mahony, J. et al., "*Lactococcus lactis* phage jj50, complete genome" Database EM PH, Sep. 15, 2006, XP-002465751.

Mahony, J. et al., "Putative uncharacterized protein" Database UniProt, Oct. 17, 2006, XP-002465578.

Mahony, J. et al., "Putative uncharacterized protein" Database UniProt, Oct. 17, 2006, XP-002465579.

Martinussen, Jan et al., "Cloning and characterization of upp, a gene encoding uracil phosphoribosyltransferase from *Lactococcus lactis*" Journal of Bacteriology, Nov. 1994, pp. 6457-6463, vol. 176, No. 21.

Moineau, Sylvain et al., "Differentiation of Two Abortive Mechanisms by Using Monoclonal Antibodies Directed toward *Lactococcal* Bacteriophage Capsid Proteins" Applied and Enviornmental Microbiology, Jan. 1993, pp. 208-212, vol. 59, No. 1.

Moineau, Sylvain et al., "Evolution of a lytic bacteriophage via DNA acquisition from the *Lactococcus lactis* chromosome" Applied and Environmental Microbiology, Jun. 1994, pp. 1832-1841, vol. 60, No. 6.

Noble, Rachel T. et al., "Rapid virus production and removal as measured with fluorescently labeled viruses as tracers" Applied and Environmental Microbiology, Sep. 2000, pp. 3790-3797, vol. 66, No. 9.

Roussel, Y. et al., "*Lactococcus lactis* subsp. *cremoris* Lin (lin) and putative transposasa gene, complete cds; putative transposase gene, partial cds; and unknown gene" Database EMBL, Mar. 9, 2001, XP-002465574.

Roussel, Y. et al., "Putative uncharacterized protein" Database UniProt, Jun. 1, 2001, XP-002465575.

Sanders, M. E. et al., "Restriction and Modification in Group N *Streptococci*: Effect of Heat on Development of Modified Lytic Bacteriophage" Applied and Environmental Microbiology, Sep. 1980, pp. 500-506, vol. 40, No. 3.

Schouler, Catherine et al., "Sequence and organization of the *Lactococcal* prolate-headed bIL67 phage genome" Microbiology, 1994, pp. 3061-3069, vol. 140.

Schouler C., et al., "Unidentified ORF8; putative; NCBI gi: 522276" Database UniProt, Nov. 1, 1996, XP-002465582.

Vossen, Jos M. B. M. Van Der et al., "Isolation and characterization of *Streptococcus cremoris* Wg2-specific promoters" Applied and Environmental Microbiology, Oct. 1987, pp. 2452-2457, vol. 53, No. 10.

Ward, Lawrence J.H. et al., "Sequence analysis of the lysine gene region of the prolate *Lactococcal* bacteriophage c2" Canadian Journal of Mircobiology, 1993, pp. 767-774, vol. 39, No. 8.

Ward, L.J. et al., "Bacteriophage c2 complete genome" Database EM PH, Jan. 4, 1996, XP-002465752.

Ward, L.J. et al., "Ell protein" Database UniProt, Nov. 1, 1996, XP-002465581.

Wegmann, Udo et al., "Complete Genome Sequence of the Prototype Lactic Acid Bacterium *Lactococcus Lactis* subsp. *cremoris* MG1363" Journal of Bacteriology, Apr. 2007, pp. 3256-3270, vol. 189, No. 8.

Wegmann, U. et al., "Putative uncharacterized protein" Database UniProt, Mar. 6, 2007, XP-002465576.

\* cited by examiner

| Name | Source | Seq.Acc.Nr | Author | seq.publ | Patent nr | Sensitive phages | EOP (range) |
|---|---|---|---|---|---|---|---|
| AbiA | pTR2030 | U17233 | Dinsmore&Klaenhammer | 1990 | WO2004020598-A2 | 936, c2, P335 | 1E-4 to 1E-8 |
| AbiB | pHP003 | AF247159 | Cluzel et al | 2000 | WO9205260-A | 936 | ? |
| AbiC | pTN20 | M95956 | Durmaz et al | 1994 | | 936, P335 | 1E-2 to 1E-4 |
| AbiD | pBF61 | U10992 | McLandsborough et al | 1995 | | 936, c2 | 1E-4 |
| AbiD1 | pIL105 | L35176 | Bidnenko et al | 1995 | | 936, c2 | 1E-4 to 1E-6 |
| AbiE | pNP40 | U36837 | Garvey et al | 1995 | | 936 | 1E-4 |
| AbiF | pNP40 | U36837 | Garvey et al | 1995 | | 936, c2 | 1E-4 to 1E-6 |
| AbiG | pCI750 | U60336 | O'Connor et al | 1996 | US5019506-A | 936, (c2), P335 | 1E-3 |
| AbiH | chromosome? | X97651 | Prevots et al | 1996 | US5955332-A | 936, (c2) | ? |
| AbiI | | U38973 | Su et al | 1997 | DE19538001-A1 | 936, (c2) | ? |
| AbiJ | pND852 | U41294 | Deng et al | 1995 | DE19538001-A1 | (936) | ? |
| AbiK | pSRQ800 | U35629 | Emond et al | 1997 | EP868514-A | 936, (c2), P335 | 1E-5 to 1E-8 |
| AbiL | pND861 | U94520 | Deng et al | 1999 | DE19538001-A1 ? | 936, (c2) | ? |
| AbiN | prophage | Y11901 | Prevots et al | 1998 | US5712150-A | 936, c2 | ? |
| AbiO | pPF144 | I61427 | Prevots et al | 1997 | US 5658770 | 936, c2 | ? |
| AbiP | pIL2614 | U90222 | Domingues et al | 1998 | | 936 | 1E-7 |
| AbiQ | pSRQ900 | AF001314 | Emond et al | 1998 | WO9928476-A | 936, c2 | 1E-8 |
| AbiR | pKR223 | AF216814 | Twomey et al | 2000 | | c2 | ? |
| AbiT | pED1 | AF483000 | Bouchard et al | 2002 | WO200281697-A | 936, P335 | 1E-5 to 1E-7 |
| AbiU | pND001 | AF188839 | Dai et al | 2001 | | (936), c2, (P335) | 1E-1 to 1E-2 |
| AbiZ | pTR2030 | U17233 | Durmaz and Klaenhammer | 2006 | US2005130126-A1 | P335 | 1E-6 |
| AbiV | chromosome and pLC5 | | Haaber et al | 2007 | | 936, c2 | 1E-4 |

Fig. 1

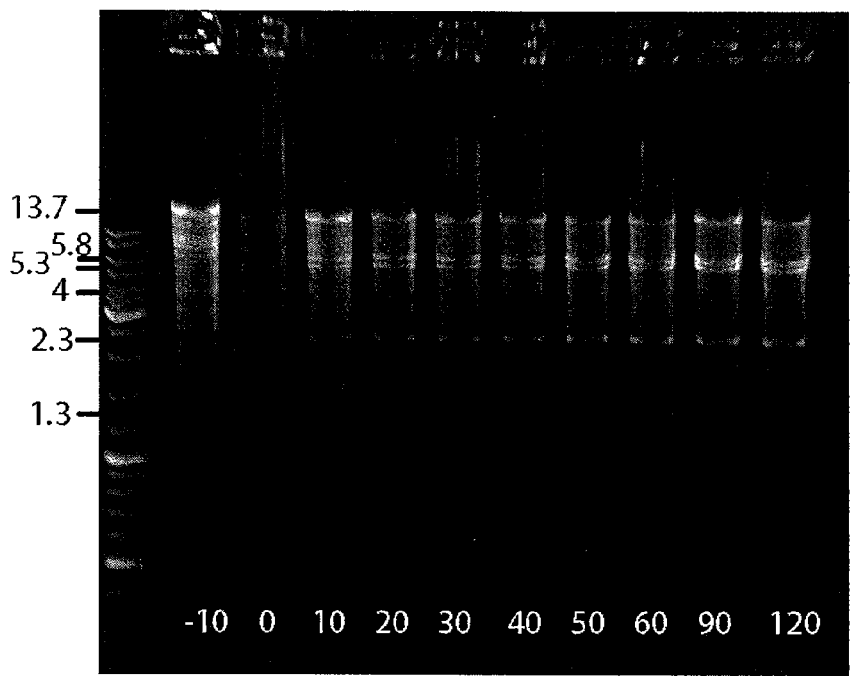
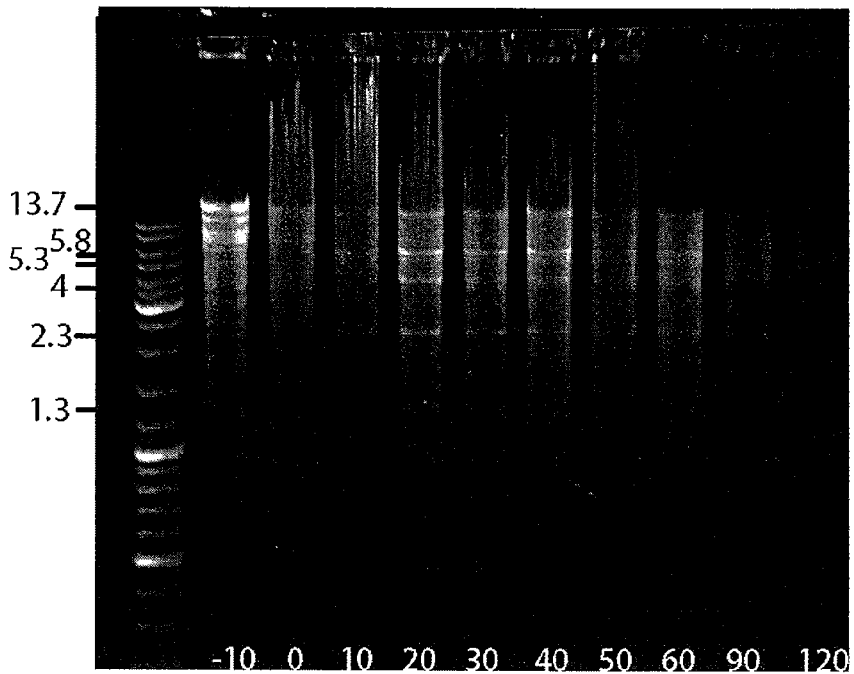
Fig. 3

```
   1 - AAAAAGAGAGTGGGTGTATCAATTTAAATATAAGAACTTTGAAGAAGCCTATCAGAGTAT  -   60
  61 - TTTCTGGTACATCGAAGCCTTTTATAATTCAAAACGAATCCATCAAAGTTTAGGGTATCT  -  120
 121 - TACACCTAATCAATTTGAAAAGGTAAGTGCTTAAAATAAATAGATTAAAATTCTACGTTT  -  180
 181 - GTTACTCTAAAAACTTGACTTAACGTCACTTCTTGAGTTAACTTCGCATAATAAAGAAAA  -  240
 241 - CAAAGACTTTTTGGATGAAATAGACAAAACTTACTCTAAAATTGATACTGTCAATACTAA  -  300
 301 - AGTTAGACAAACTGAAGTAGCTGCAACTACTAATCAACTTGCGCTAACTAAAGCAAATGT  -  360
 361 - ACAAATTCATACCCTTTTAGTAATTGCTAGTAATTATTATCAATCAGTATGGATCCAGAT  -  420
 421 - TAAAGAATGAACGGAGAGTTTTATGTTTGATAAAGACAACTATGCATTAGGAAAAATGAA  -  480
   1 -          RBS         M  F  D  K  D  N  Y  A  L  G  K  M  K   -   13
 481 - GAATACCCTTAATACCAAAGAAAGTAAGTTTTCTCTAAAGTCAACTGATGATCTTAATAA  -  540
  14 -  N  T  L  N  T  K  E  S  K  F  S  L  K  S  T  D  D  L  N  K   -   33
 541 - ATGCATCGATCATATTTCAGTCTTAATAAAAGATGCATATCTGCTTTATACGAATGAATC  -  600
  34 -  C  I  D  H  I  S  V  L  I  K  D  A  Y  L  L  Y  T  N  E  S   -   53
 601 - ATTTGCCACTTCTACATTCATTTCAATAACAATTATTGAAGAAGTTGGTAAAACTCATAT  -  660
  54 -  F  A  T  S  F  I  S  I  T  I  I  E  E  V  G  K  T  H  I    -   73
 661 - AGGTATGTTTATCAGTGAGAATAAAGATATAAAGCGTGGGAAAGACCCTTTGAGAAATCA  -  720
  74 -  G  M  F  I  S  E  N  K  D  I  K  R  G  K  D  P  L  R  N  H   -   93
 721 - TAAATCCAAACACGCTTTTGGATCTCTTCCAACTATAAAAATGGGAGGACGACTTAATAA  -  780
  94 -  K  S  K  H  A  F  G  S  L  P  T  I  K  M  G  G  R  L  N  K   -  113
 781 - GGCTATTGGAGATGAAATGATTGATAAAATCGTCGAAGATGCCGAAACTGGTGAACTTAT  -  840
 114 -  A  I  G  D  E  M  I  D  K  I  V  E  D  A  E  T  G  E  L  I   -  133
 841 - TTCAATACGGGAGTCATCTTTGTATGCAGATATTATTGATGATATTCTTGAAGTACCTAG  -  900
 134 -  S  I  R  E  S  S  L  Y  A  D  I  I  D  D  I  L  E  V  P  S   -  153
 901 - TGAAAAAATTAGTAAAGAACAAAGTAGAGCATTGCTCCTTTATGCGATAGAATGTTTTGA  -  960
 154 -  E  K  I  S  K  E  Q  S  R  A  L  L  L  Y  A  I  E  C  F  D   -  173
 961 - TGACAGTTTAGTTGGCTATACACATCATTCATTTGAAGTATCAGAGACAACTGATGAGTT  - 1020
 174 -  D  S  L  V  G  Y  T  H  H  S  F  E  V  S  E  T  T  D  E  L   -  193
1021 - GTTTGAAAAGTTAGCAAACAATAAATAGTTAAATCTTGAGTTTGATTTTGCTGAATATTC  - 1080
 194 -  F  E  K  L  A  N  N  K  *                                    -
1081 - TGCATTTATCGGGCGGAATGATGCCCTTAGACTTTGCAACAGAACCTCGATTTTAATTCG  - 1140
1141 - TTCAGAATAGGTTATACTAGACAAAAGATCGGCTCCTAAAAATGGGTTTGTGATAAACAC  - 1200
1201 - CATTTTAAAGGAAGCTGGTCTTTTTTTGTCCAAACACTGGTCAGACAATTTTGGGGCCTAT  - 1260
1261 - GATATTTGGTGTTGATAGATAAAATTCATCAACACTATTC                      - 1300
```

Underlined sequence is Ribosome Binding Site (RBS)

Fig. 4 orf26 (sav) and upstream region after orf27 stop codon

```
  1 - AAGATACAGTAAAAACTTTAATGATAGCTGTAGGTATAGGCTTTACACTTATCGCTATCA -  60

61 - CTTGGATAGGTATAATTGCAACGTTGCTTATTACATGGATTGGGGGTAACATCTAATGAA - 120
  1 -                                      RBS              M  N -   2

121 - TTATGGTACAAATAAGCACTATGCCAATGAATACGGTATGGAACTTAACGAATACTTTAA - 180
  3 -  Y  G  T  N  K  H  Y  A  N  E  Y  G  M  E  L  N  E  Y  F  K -  22

181 - ACATCATTTTAGCTATGAAGAGCTTGCAGGCTGGTATACAATGCAGGTATTAAAGTATCT - 240
 23 -  H  H  F  S  Y  E  E  L  A  G  W  Y  T  M  Q  V  L  K  Y  L -  42

241 - AGTGAGAGCTGGCAAGAAAGAGGGTGAAAGCTACGACAAAGACCGTAACAAGGCTTTAGA - 300
 43 -  V  R  A  G  K  K  E  G  E  S  Y  D  K  D  R  N  K  A  L  D -  62

301 - CTATGCAGGAGAACTTGCTAACTTAAGTAACGAGAATGAGCTTACAGAATACACTACTGA - 360
 63 -  Y  A  G  E  L  A  N  L  S  N  E  N  E  L  T  E  Y  T  T  D -  82

361 - CGACATTATGGGCTTTGCACAAGATATAGCTGATGATTTCAAACAATGGAAAGGCGAAAG - 420
 83 -  D  I  M  G  F  A  Q  D  I  A  D  D  F  K  Q  W  K  G  E  R - 102

421 - AAATAACTTTAAATCAGAGTTCACGAAAGAAGAGATAAAAGCGATTGATGAAAGATACTT - 480
103 -  N  N  F  K  S  E  F  T  K  E  E  I  K  A  I  D  E  R  Y  L - 122

481 - GGAATTTATTGAAGAGGTC                                          - 499
123 -  E  F  I  E  E  V                                           - 128
```

Fig. 5

PHAGE RESISTANCE

CROSS REFERENCE TO RELATED APPLICATIONS

This application claims the benefit and priority to and is a U.S. National Phase Application of PCT International Application Number PCT/DK2008/050166, filed on Jul. 2, 2008, designating the United States of America and published in the English language, which is an International Application of and claims the benefit of priority to European Patent Application No. 07111640.4, filed on Jul. 3, 2007, and U.S. Provisional Application No. 60/947,759, filed on Jul. 3, 2007. The disclosures of the above-referenced applications are hereby expressly incorporated by reference in their entireties.

TECHNICAL FIELD OF THE INVENTION

The present invention relates to the field of dairy science. In particular the present invention relates to methods for improving dairy starter culture quality.

BACKGROUND OF THE INVENTION

The lactic acid bacterium *Lactococcus lactis* is used in milk fermentations world wide in the dairy industry to produce a variety of cultured dairy products. Phage infections can ruin the fermentation by inactivating the inoculated cultures. Phages are the major cause of fermentation failures during the manufacture of these cultured dairy products. There is thus a permanent need in the art for *L. lactis* starter cultures to perform at a high level of consistency and efficiency.

Phages

Lactococcal phages are characterized by having relatively short latent periods and relatively large burst sizes. They are the major cause of fermentation failure leading to production loss in the dairy industry. Lactococcal phages are currently divided into eight distinct groups of which three groups namely "936", "c2" and "P335" are responsible for the vast majority of phage attacks in industrial fermentations. The genomes of the phages within one single group are highly conserved except for the P335 group.

Industrial fermentations are carried out in large fermentation vats in a non-sterile environment. Prior to fermentation, the ingredients are usually pasteurized. However, the phages are often resistant to the pasteurization process. Presence of phages can lead to variations in flavor and texture of the fermented dairy product or even loss of the entire production with serious economical loss as a consequence. The dairy industry is therefore using a variety of methods in limiting phage attacks. Such approaches include e.g. improved disinfection processes, rotation of starter cultures and application of phage resistant starter strains.

Phage Defense Mechanisms

During evolution *L. lactis* has developed a series of defense mechanisms against phage attacks. These naturally occurring phage resistance mechanisms (φrm) has been studied extensively and also applied in industrial starter cultures. Most of the naturally occurring φrms are found on plasmids and they are classified into four groups according to their mode of action: 1) adsorption inhibition, 2) blocking of phage DNA injection, 3) restriction/modification systems (R/M) and 4) abortive infection mechanisms (Abi). Among these defense mechanisms, the Abi systems are considered to be the most powerful due to their diverse mode of action and efficiency against the most common phages.

Abi Mechanisms

Abi mechanisms function in the phage life cycle subsequent to the injection of phage DNA into the bacterial cell—typically after expression of early phage genes. As a consequence, the phage lytic cycle is terminated and usually the host dies. Very few viable phage progeny are thus released and the phenotypic outcome is a reduction in the number and size of plaques and thus a reduction of the severity of the phage infection.

To date, twenty-two lactococcal Abi systems have been isolated. These Abi systems target one, two or all three groups of the common phage species 936, c2, P335 with varying efficiency (EOP values from $10^{-1}$ to $<10^{-8}$) (FIG. 1).

Most of the isolated Abi systems are found on plasmids of which many are conjugative. By sharing the φrms within the bacterial population, conjugation thus provides an adaptation strategy to the phage containing dairy environment. Only a few abi mechanisms have been isolated from the chromosome of *L. lactis*. This may partly be due to the fact that it is generally easier to isolate genes present on plasmids compared to isolation of genes present on chromosomes. The procedure used in the present invention to isolate a φrm from the chromosome of *L. lactis* can be used to identify other φrms on the bacterial chromosome.

By isolating spontaneous phage resistant mutants with a similar phenotype with regards to efficiency against a range of phage species it is probably possible to identify strains expressing the abi without having to use genetic modification. Using this method, non-GMO phage resistant strains can thus be isolated. Use of non-GMO starter cultures may be an advantage in some case, in particular in relation to the fact that the legislation in some countries does not allow use of GMO. Furthermore, some consumers tend to prefer non-GMO derived products.

The point of interference with the phage life cycle has been determined to some degree for most of the Abi mechanisms:

AbiA, AbiF, AbiK, AbiP, AbiR, and AbiT apparently interfere with phage DNA replication.

AbiC apparently interfere with capsid production.

AbiE, AbiI, and AbiQ apparently interfere with phage packaging.

AbiB is apparently an RNase.

AbiD1 seems to interfere with a phage RuvC-like endonuclease.

AbiU apparently delays phage transcription.

AbiZ apparently causes premature lysis of the infected cell.

These very diverse modes of action are most likely the reason for the very low degree of protein homology that exists between the different Abi mechanisms.

Though the point of action in the phage life cycle has been determined, the phage protein interacting with the Abi mechanism has only been identified in AbiA, AbiD1, AbiK and AbiP. An increasing number of phage genomes are being sequenced providing a bulk of sequence data in which numerous putative proteins are found. However, experimental evidence for the function of these proteins are lacking behind.

Several phage resistant strains of *L. lactis* have been constructed by introducing abi systems in phage sensitive industrial starter cultures. However, extensive use of these bacterial cultures leads to problems with emergence of phage mutants capable of overcoming the introduced abi systems.

The evolutionary "arms race" between phage mutants and bacterial φrms means that there is a constant need in the art for identifying novel natural φrms. There is a particular need in the art for finding novel Abi-mechanisms that interact with previously unknown targets in the phage. Furthermore there is a need in the art for novel Abi-mechanisms in *Lactococcus* bacteria that do not classify as GMO. Finally there is a need in the art for identifying φrms that provide efficient protection against phages.

SUMMARY OF THE INVENTION

The present invention thus relates to a polynucleotide conferring at least one phage resistance mechanism to a *Lactococcus* bacterium, wherein said polynucleotide encodes a polypeptide according to SEQ ID NO 1 and/or SEQ ID NO 2, and/or SEQ ID NO7 or a fragment or variant thereof. The present invention furthermore relates to the polypeptides, uses thereof, expression vectors and cells expressing these polypeptide sequences. The present invention also relates to methods for producing fermented dairy products as well as the products resulting from these processes.

The present invention finally relates to methods for identifying φrms on chromosomal DNA.

The novel φrm(-s) according to the present invention provide a number of advantages as described in the following.

BRIEF DESCRIPTION OF THE FIGURES

FIG. 1: Characteristics of the twenty-two (including AbiV from the present invention) Abi mechanisms isolated to date.

FIG. 2A: the strains with the transposon containing vector pGhost9::ISS1 inserted on the chromosome. Arrows indicate the position and direction of the inserted ISS1 sequences. The presence of a promoter and the φrm⁺ phenotype is indicated to the right. FIG. 2B: the strains with the cloned fragment including orf1. The lines represent the cloned DNA fragment, and the x in JH-24 represent the position of the frame shift mutation introduced into this strain.

FIG. 3: Time course experiment of a phage infection. Samples are taken during infection of phage resistant *Lactococcus lactis* strain JH-20 (upper panel) and phage sensitive *Lactococcus lactis* strain JH-16 (lower panel) with p2 phage. The experiment was run for 120 min and samples were taken at: −10, 0, 10, 20, 30, 40, 50, 60, 90 and 120 minutes. Total DNA was isolated from the cells and restricted with EcoRI. The resulting restriction fragments are representing EcoRI digested p2 DNA. Band 1.3 kb and 4 kb are spanning the cos site which marks the extremities of the phage DNA. The cos site is cut during packaging of phage DNA in the lytic life cycle of the wt phage, revealing mature phage DNA molecules in units of one genome. In the phage resistant Abi mutant, the cos site is not cut resulting in non-mature phage DNA that can not be packed into the phage capsids. The figure thus shows that production of mature phage DNA is significantly decreased in the strains containing the AbiV mechanism.

FIG. 4: DNA sequence of the 1.3 kb DNA fragment (bp 1021-2320 in GenBank acc.nr AF324839) cloned in vector pJH2. This fragment comprises orf1 (bp 1276-1878) encoding the φrm (SEQ ID NO: 1). Ribosome binding site is underlined in nucleotides matching the lactococcal consensus sequence (AGAAAGGAGGT) SEQ ID NO: 19. The translated amino acids are shown below the DNA sequence.

FIG. 5: DNA sequence of the 499 bp DNA fragment from phage p2 containing orf26 and the upstream region towards orf27. Ribosome binding site is underlined in nucleotides matching the lactococcal consensus sequence (AGAAAGGAGGT) SEQ ID NO: 19. The translated amino acids are shown below the DNA sequence (SEQ ID NO: 2).

DETAILED DESCRIPTION OF THE INVENTION

Definitions

Figure 2:
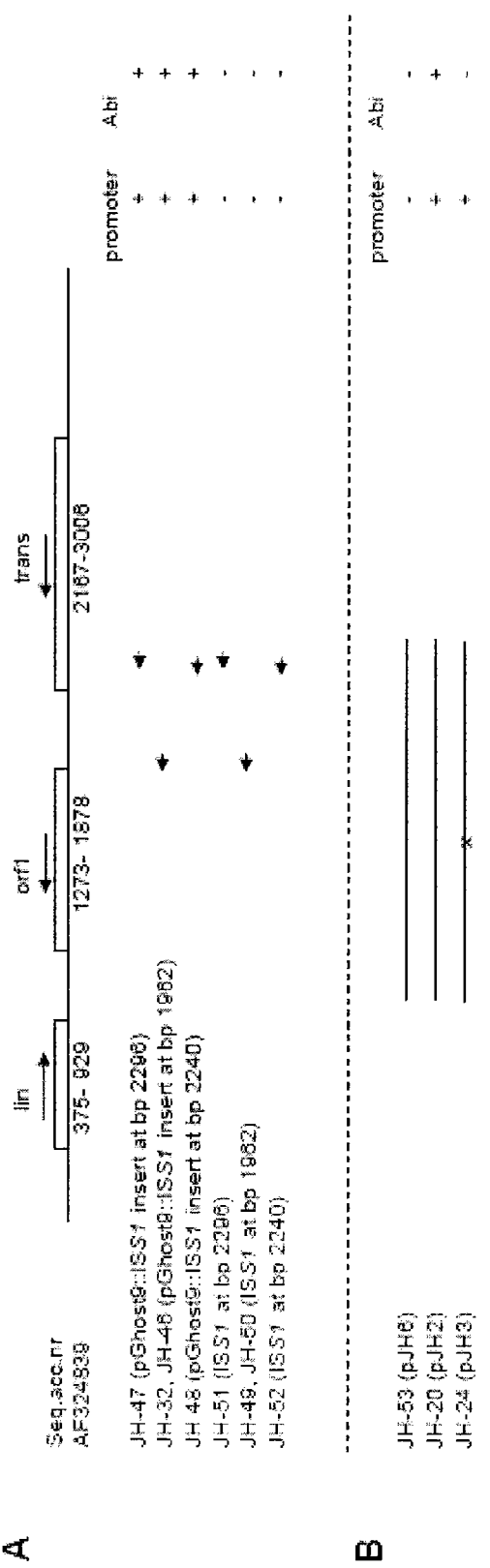
FIG. 2: The sequence from GenBank (acc.nr AF324839) containing orf1 which surprisingly turned out to have the capability to function as a φrm according to the present invention.

Prior to discussing the present invention in further details, the following terms and conventions will first be defined:

Phages: A bacteriophage (from 'bacteria' and Greek phagein, 'to eat') is any one of a number of virus-like agents that infect bacteria. The term is commonly used in its shortened form, phage. Typically, bacteriophages consist of an outer protein shell (called capsid or head) enclosing genetic material. The genetic material can be ssRNA, dsRNA, ssDNA, or dsDNA between 5 and 500 kilo base pairs long with either circular or linear arrangement. Bacteriophages are much smaller than the bacteria they destroy—usually between 20 and 200 nm in size. Phages according to the present invention have the ability to infect bacteria of the genus *Lactococcus*.

Phage resistance mechanism: A functional phage resistance mechanism is herein meant to be a mechanism that directly inhibits the phage lytic life cycle. However, phage resistance mechanisms as used herein furthermore denote mechanisms that works in synergy with a phage encoded product. As an example hereof, the present invention relates to use of SEQ ID NO 1 for conferring phage resistance to bacterial cells as well as the use of SEQ ID NO 1 in combination with SEQ ID NO 2 for obtaining an even more efficient phage resistance mechanism than was possible when only using SEQ ID NO 1.

*Lactococcus*: is a lactic acid bacterial genus of five major species formerly included as members of the genus *Streptococcus* Group N and related species. They are gram-positive bacteria, and they are typically spherical or ovoid, 0.5-1.2 μm by 0.5-1.5 μm, and occur in pairs and short chains. They are non-spore forming and are not motile. The type species for the genus is *L. lactis* which in addition have two subspecies *lactis* and *cremoris*. *Lactococcus* is commonly used in the dairy industry in the manufacture of fermented dairy products. They can be used in single strain starter cultures, or in mixed strain cultures comprising other strains of *Lactococcus* or lactic acid bacteria such as e.g. *Leuconostoc, Lactobacillus* and *Streptococcus*.

A fragment: A fragment according to the present invention is herein defined as a fragment of a polypeptide being at least 100 amino acids, preferably at least 110, more preferably at least 120 amino acids. With regards to SEQ ID NO 1, the fragment is preferably at least 100 amino acids in length, more preferably at least 125 amino acids in length, more preferably at least 150 amino acids in length, more preferably at least 175 and most preferably at least 190 amino acids in length.

Promoter: The term "promoter", "promoter region" or "promoter sequence" refer generally to transcriptional regulatory regions of a gene, which may be found at the 5' or 3' side of the coding region, or within the coding region, or within introns. As used herein the term promoter shall include any portion of genomic DNA (including genomic DNA disclosed herein), which is capable of initiating expression of but not limited to operably linked nucleotide sequences at levels detectable above background. In the context with the present invention a "strong promoter" shall be understood as a promoter which results in expression of a polypeptide according to the invention, wherein the level of expression is significantly higher compared to the endogenous homologous promoter in the *Lactococcus* genome. The level of expression can be detected and/or measured by e.g. Northern blot, real-time PCR, reporter gene assays, etc.

Expression vector: A vector is a component or composition for facilitating cell transduction or transfection by a selected nucleic acid, or expression of the nucleic acid in the cell. Vectors include, e.g., plasmids, cosmids, viruses, BACs, PACs, P1, YACs, bacteria, poly-lysine, as well as linear nucleotide fragments etc. An "expression vector" is a nucleic acid construct or sequence, generated recombinantly or synthetically, with a series of specific nucleic acid elements that permit transcription of a particular nucleic acid sequence in a host cell. The expression vector can be part of a plasmid, virus, or nucleic acid fragment. The expression vector typically includes a nucleic acid to be transcribed operably linked to a promoter. The nucleic acid to be transcribed is typically under the direction or control of the promoter. The expression vector may replicate autonomously in the host cell or may integrate into the host genome after the transfection or transduction and replicate as part of the genome. Finally "an expression vector" encoding more than one polypeptide sequences according to the present invention comprises the situation wherein one expression vector comprises polynucleotide sequences encoding more than one polypeptide product as well as the situation wherein the polynucleotide sequences are cloned into two different expression vectors.

pGhost9::ISS1: The term "pGhost9::ISS1" covers a vector with an antibiotic resistance marker, a *Lactococcus* replicon, and preferably also an *E. coli* replicon. The replicon is thermosensitive allowing for selection for integration into the host chromosome. Also the vector contains an insertion sequence that enables random integration of the vector into the host chromosome. It follows that vectors with similar functions may be used in connection with the present invention.

Identity: The term "identity" or "sequence identity" is a measure of the degree of identity between polynucleotide sequences on a nucleotide-by-nucleotide basis or amino acid-by-amino acid basis, respectively over a window of comparison. Sequences according to the present invention have an identity of at least 70% to SEQ ID NO 1, or a fragment thereof.

Food products: Food products according to the present invention include milk based products that have been subject to fermentation processes. Examples thereof include: sour cream, crème fraîche, buttermilk, butter, cheese, cottage cheese, quark, cream cheese, fromage frais, yoghurt, etc. However, other types of food products may also be produced using fermentation or fermentative microorganisms according to the present invention such as e.g. fruit juices, fermented vegetables/fruits, processed meat products, etc.

It should be noted that embodiments and features described in the context of one of the aspects of the present invention also apply to the other aspects of the invention.

In a first aspect the present invention thus relates to an isolated polynucleotide sequence that encodes a polypeptide with at least 70% identity, preferably at least 75% identity, more preferably at least 80% identity, more preferably at least 85% identity, more preferably at least 70% identity, preferably at least 75% identity, more preferably at least 80% identity, more preferably at least 85% identity, more preferably at least 90% identity, and most preferably at least 95% identity with SEQ ID NO 1 (AbiV from *Lactococcus lactis*), or a fragment thereof, and wherein expression of said polynucleotide confers at least one phage resistance mechanism to a *Lactococcus* bacterium. This polynucleotide sequence is found naturally in the *Lactococcus* bacterium, but it is normally not transcriptionally active. It has surprisingly been found that expression of this polypeptide confers a previously unknown phage resistance mechanism to the bacterium.

A second aspect of the present invention relates to an isolated polynucleotide derived from a *Lactococcus lactis* phage that encodes a polypeptide with at least 70% identity, preferably at least 75% identity, more preferably at least 80% identity, more preferably at least 85% identity, more preferably at least 95% identity, preferably at least 97% identity, and most preferably at least 99% identity with SEQ ID NO 2, or a fragment thereof and/or an isolated polynucleotide that encodes a polypeptide with at least 70% identity, preferably at least 75% identity, more preferably at least 80% identity, more preferably at least 85% identity, more preferably at least 95% identity, preferably at least 97% identity, and most preferably at least 99% identity with SEQ ID NO 7. Optionally, the polynucleotide sequence may encode at least one of SEQ ID NO 1, SEQ ID NO 2, and SEQ ID NO 7 or any variant thereof in the form of one or more polynucleotide sequences.

SEQ ID NO 2 and SEQ ID NO 7 are phage proteins. The inventors have found out that these proteins most likely need to be mutated in order for the phage to escape the phage resistance mechanism conferred by expression of SEQ ID NO 1 or variants thereof. Phage proteins according to the present invention therefore have at least 70% identity with SEQ ID NO 2 and/or SEQ ID NO 7 in order to provide functional phage protein that may suppress the effects of emergence of mutated phage protein that could potentially suppress the effects of the translated SEQ ID NO 1 protein or variants thereof. In a preferred embodiment according to the present invention, polynucleotide sequences encoding both SEQ ID NO 1 or variants thereof as well as SEQ ID NO 2 and/or SEQ ID NO 7 or variants thereof, are thus provided thus conferring highly efficient phage protection mechanisms to a host cell. It furthermore follows that the invention relates to expression vectors as well as *Lactococcus* bacteria and/or starter cultures comprising polynucleotide sequences encoding such polypeptide sequences.

In a third aspect, the present invention relates to an isolated polypeptide conferring at least one phage resistance mechanism to a *Lactococcus* bacterium, wherein said polypeptide is selected from one or more of the group consisting of: a polypeptide with at least 70% identity with SEQ ID NO 1, or a fragment thereof, a polypeptide with at least 70% identity with SEQ ID NO 2, or a fragment thereof, and a polypeptide with at least 70% identity with SEQ ID NO 7, or a fragment thereof.

A fourth aspect relates to the use of one or more polynucleotides according to the present invention and/or one or more polypeptides according to the present invention for improving phage resistance in a *Lactococcus* bacterium.

A fifth aspect relates to a method for fermenting food product, said method comprising the step of adding one or more of the components according to the present invention. The invention furthermore relates to products that can be obtained and/or are obtained using this method.

A sixth aspect relates to a method for obtaining phage resistant bacterial cells, said method comprising use of pGhost9::ISS1 (or similar systems) for random insertion into a bacterial cell and subsequently screening and selecting for phage resistant cells. The invention furthermore relates to cells that can be obtained and/or are obtained by such methods. In a preferred embodiment, the cell is a *Lactococcus* bacterium wherein a polynucleotide encoding SEQ ID NO 1 (or a variant thereof) is transcriptionally active.

A final aspect relates to a *Lactococcus* bacterium that expresses at least one polypeptide selected from the group consisting of: a polypeptide with at least 70% identity with SEQ ID NO 1, or a fragment thereof, a polypeptide with at least 70% identity with SEQ ID NO 2, or a fragment thereof, and a polypeptide with at least 70% identity with SEQ ID NO 7, or a fragment thereof.

All patent and non-patent references cited in the present application, are hereby incorporated by reference in their entirety.

The invention will now be described in further details in the following non-limiting examples.

EXAMPLES

Example 1

Bacterial Strains, Plasmids, and Media

Strains and plasmids used in this invention are listed in table 1. *Escherichia coli* was grown at 37° C. in LB medium. *Lactococcus lactis* was grown in M17 with the supplement of 0.5% glucose (GM17). Lactococci were grown at 30° C. except strains containing the thermo sensitive vector pGhost9::ISS1. These strains were grown at 28° C. for replication of the vector or 36° C. to avoid replication. When appropriate, antibiotics were added as follows: *E. coli*, 100 µg/ml of ampicillin, 10 µg/ml of chloramphenicol, 150 µg/ml of erythromycin; for *L. lactis*, 5 µg/ml of chloramphenicol, 3 µg/ml of erythromycin.

TABLE 1

List of bacteria, phages and plasmids used in the invention

| Bacterial strain, phage or plasmid | Characteristic | Source |
|---|---|---|
| *Lactococcus lactis* | | |
| SMQ-86 | *Lactococcus lactis* subsp. *cremoris*. Multiple plasmids, pSA3, host for the tested P335 phages. Erm$^R$ | (2) |
| IL1403 | *Lactococcus lactis* subsp. *lactis* IL1403, host for some 936 phages | (1) |
| MB112 | *Lactococcus lactis* subsp. *cremoris* MG1363, Δupp, Host for 936 and c2 phages | (7) |
| JH-20 | MB112 (pJH2); Cam$^R$, Abi$^+$ | This Invention |
| JH-22 | IL1403 (pJH2); Cam$^R$, Abi$^+$ | This Invention |
| JH-23 | SMQ-86 (pJH2); Cam$^R$, Abi$^+$ | This Invention |
| JH-24 | MB112 (pJH3); Cam$^R$, Abi$^-$ | This Invention |
| JH-25 | MB112 (pJH4); Cam$^R$, Abi$^+$ | This Invention |
| JH-26 | MB112 (pJH5); Cam$^R$, Abi$^+$ | This Invention |
| JH-32 | MB112 (pGhost9::ISS1 inserted in Lin at bp1962); Erm$^R$, grown at 36° C., Abi$^+$ | This Invention |
| JH-46 | MB112 (pGhost9::ISS1 inserted in Lin at bp1962); Erm$^R$, grown at 36° C., Abi$^+$ | This Invention |
| JH-47 | MB112 (pGhost9::ISS1 inserted in Lin at bp2296); Erm$^R$, grown at 36° C., Abi$^+$ | This Invention |
| JH-48 | MB112 (pGhost9::ISS1 inserted in Lin at bp2240); Erm$^R$, grown at 36° C., Abi$^+$ | This Invention |
| JH-49 | JH-32 cured for pGhost9, leaving ISS1 in place; Abi$^-$ | This Invention |
| JH-50 | JH-46 cured for pGhost9, leaving ISS1 in place; Abi$^-$ | This Invention |
| JH-51 | JH-47 cured for pGhost9, leaving ISS1 in place; Abi$^-$ | This Invention |
| JH-52 | JH-48 cured for pGhost9, leaving ISS1 in place; Abi$^-$ | This Invention |
| JH-53 | MB112 (pJH6); Cam$^R$, Abi$^-$ | This Invention |
| JH-54 | MB112 (pLC5); Cam$^R$, Abi$^-$ | This Invention |
| JH-80 | MB112 (spontaneous mutation to express φrm); Abi$^+$ | This Invention |
| JH-81 | transconjugant with transferred φ rm and Erm$^R$ from JH-32 to LKH208; Abi$^+$, Erm$^R$, Rif$^R$, Strep$^R$, FU$^S$ | This Invention |
| MG1614 | MG 1363 Rif$^R$, Strep$^R$ (M. Gasson) | (5) |
| *Escherichia coli* | | |
| EC1000 | RepA$^+$ MC1000, Km$^R$ | (4) |
| JH-56 | EC1000 (pJH7), Erm$^R$ | This Invention |
| JH-57 | EC1000 (pJH8), Erm$^R$ | This Invention |
| JH-58 | EC1000 (pJH9), Erm$^R$ | This Invention |
| JH-59 | EC1000 (pJH10), Erm$^R$ | This Invention |
| TOP10F' | Chemically competent cells from the TOPO TA cloning kit | Invitrogen |
| JH-19d | EC1000 (pJH6), Cam$^R$ | This Invention |
| phages | | |
| p2 | Small isometric headed, 936 species | S. M |
| sk1 | Small isometric headed, 936 species | F. V |
| jj50 | Small isometric headed, 936 species | F. V |
| 712 | Small isometric headed, 936 species | S. M |
| P008 | Small isometric headed, 936 species | S. M |
| bIL170 | Small isometric headed, 936 species | S. M |
| c2 | Prolate headed, c2 species | S. M |
| bIL67 | Prolate headed, c2 species | S. M |
| ml3 | Prolate headed, c2 species | S. M |
| eb1 | Prolate headed, c2 species | S. M |
| ul36 | Small isometric headed, P335 species | S. M |
| KITI | Small isometric headed, P335 species | S. M |
| Ø31 | Small isometric headed, P335 species | S. M |
| Ø50 | Small isometric headed, P335 species | S. M |
| Q33 | Small isometric headed, P335 species | S. M |
| Q30 | Small isometric headed, P335 species | S. M |
| P335 | Small isometric headed, P335 species | S. M |
| p2.1 | Small isometric headed, 936 species, deletion in orf26 | This Invention |
| sk1.1 | Small isometric headed, 936 species, nonsense mutation in orf26 | This Invention |

TABLE 1-continued

List of bacteria, phages and plasmids used in the invention

| Bacterial strain, phage or plasmid | Characteristic | Source |
|---|---|---|
| jj50.1 | Small isometric headed, 936 species, nonsense mutation in orf25 (homologue to p2 orf26) | This Invention |
| P008.1 | Small isometric headed, 936 species, nonsense mutation in orf33 (homologue to p2 orf26) | This Invention |
| bIL170.1 | Small isometric headed, 936 species, nonsense mutation in e24 (homologue to p2 orf26) | This Invention |
| c2.1 | Prolate headed, c2 species, mutation in e11 (homologue to p2 orf26) | This Invention |
| plasmids | | |
| pCI372 | Shuttle vector for *E. coli* and *L. lactis*. No promoter in front of multiple cloning site; Cam$^R$ | (3) |
| pLC5 | Expression vector for *L. lactis* and *E. coli*. Promoter in front of PstI site used for cloning; Cam$^R$ | This Invention |
| pGhost9::ISS1 | pGhost9::ISS1, temperature sensitive vector with insertion sequence used for random mutagenesis, Erm$^R$ | (6) |
| pJH2 | bp 1021-2320 on Lin sequence* cloned in PstI site of pLC5; Cam$^R$ | This Invention |
| pJH3 | pJH2, restricted in ClaI site of AbiV and filled with Klenow, gives frameshift mutation; Cam$^R$ | This Invention |
| pJH4 | pJH2 isolated from JH22 | This Invention |
| pJH5 | pJH2 isolated from JH23 | This Invention |
| pJH6 | bp 1021-2320 on Lin sequence* cloned in PstI and XbaI sites of pCI372 | This Invention |
| pJH7 | HindIII rescue of pGhost9::ISS1 with flanking chromosomal DNA from JH-32 | This Invention |
| pJH8 | HindIII rescue of pGhost9::ISS1 with flanking chromosomal DNA from JH-46 | This Invention |
| pJH9 | HindIII rescue of pGhost9::ISS1 with flanking chromosomal DNA from JH-47 | This Invention |

Lin sequence refers to GeneBank acc nr AF324839
Cam$^R$, chloramphenicol resistance;
Amp$^R$, ampicillin resistance;
Erm$^R$, Erythromycin resistance;
Km$^R$, Kanamycin resistance;
Rif$^R$, Rifampicin resistance;
Strep$^R$, Streptomycin resistance;
FU$^R$ fluorouracil resistance
Abi$^+$, phage resistance phenotype;
Ab$^-$, phage sensitive phenotype
F. V = Finn K. Vogensen, University of Copenhagen
S. M = Sylvain Moineau Example 2

Bacteriophage Propagation and Assays

Bacteriophages used in this invention are listed in table 1. Bacteriophages sk1 and jj50 were kindly provided by F. K. Vogensen (University of Copenhagen). Prior to use all phages were purified two times by picking a single plaque with a sterile Pasteur pipette and plating it on a sensitive host. Propagation of phages to obtain high titer lysates was performed in two steps:

In the first propagation a single plaque was transferred into a fresh ON culture of a sensitive host inoculated (1%) in GM17 supplemented with 10 mM CaCl$_2$ and incubated at 30° C. (or 36° C. in the case of pGhost9::ISS1 containing host strains) until lysis. The lysate was filtered through a 0.45 μm syringe filter.

The second propagation was performed by inoculating an exponentially growing host culture at OD$_{600}$=0.2 with phages from the first propagation (10$^4$ pfu/ml) in GM17+10 mM CaCl$_2$.

The culture was then incubated with agitation (200 rpm) until lysis at the same temperature as for the first propagation. The lysate was filtered (0.45 μm filter). The titer of phage lysates was determined using conventional methods.

Efficiency of plaquing (EOP) was calculated by dividing the titer on the tested strain with the titer on the sensitive wt strain. Adsorption assays were conducted as described by Sanders and Klaenhammer (17) except a 5 min incubation period was used instead of 15 min. Cell survival was assayed by the method of Behnke and Malke (2) using a multiplicity of infection (MOI) of 5. One-step growth assay (and determination of burst size) and center of infection (COI) assay was performed as described previously (14) by using MOIs of 0.2 and 0.5, respectively. ECOI (efficiency of COI) was determined by dividing the number of COI from the resistant strain by the number of COI from the sensitive strain. Replication of phage DNA was followed in a time course experiment using the method of Hill et al. (8). Visualization of phage DNA by labeling with the fluorescent dye SYBR-Gold was performed as described by Noble and Fuhrman (15) with the following modifications: The original SYBR-Gold solution was diluted (×1000). Phage lysate to be stained was treated with 1 μg/ml DNAse and RNAse and incubated for 30 min at 37° C. The lysate was stained with the diluted SYBR-Gold to give 2.5% final concentration (vol/vol) diluted SYBR-Gold and left ON at 4° C. in the dark. One μl of the labeled phage stock was mixed with 1 μl exponentially growing cell culture and visualized under a Zeiss axioplan epifluorescence microscope.

Example 3

Mutagenesis with pGhost9::ISS1

Random integration of the vector pGhost9::ISS1 into the chromosome of MB112 and subsequent cloning of flanking chromosomal DNA was performed essentially using the method of Maguin et al. (10). The method of Maguin, however, is normally used to identify inactivation of genes by randomly inserting the construct in chromosomal genes, thereby inactivating them. Subsequent selection for a desired phenotype enables screening for strains containing a loss of function mutation. The fact that all inspected mutants in the present invention had insertions in non coding regions or genes upstream of orf1 together with the observation that presence of the complete vector pGhost9::ISS1 was needed for the Abi$^+$ phenotype led to the hypothesis that the abiV gene (orf1) was transcribed from the promoter encoding the erythromycin resistance gene in pGhost9::ISS1 (FIG. 2). Previous studies have reported promoter activity in the ISS1 sequence (5). No effect on phage resistance phenotype of such promoter activity was observed in the present invention. It has not previously been shown that random insertion of the vector and subsequent transcription from the promoter of the erythromycin resistance gene can be used to activate existing biological mechanisms, such as e.g. Abi-mechanisms.

To ensure that the mutations in the isolated strains had arisen from independent events, the integration step (growth at 37° C.) was performed on 12 separate cultures. After the integration step, the cultures were diluted ×10.000 in GM17+3 µg/ml Erythromycin and left for phenotypic expression ON at 37° C. These cultures were inoculated (1%) and when growing exponentially aliquots were removed. 10 mM $CaCl_2$ (final concentration) was added to these aliquots before inoculating with phage sk1 (MOI>1). After 10 min incubation at 37° C. the cultures were spread on selective GM17+ Erm plates. A number of phage resistant colonies were isolated and purified from each of the 12 independent cultures. Four strains were chosen from independent cultures to identify the location of the inserted pGhost9::ISS1. This was performed by rescuing of the inserted vector and cloning of flanking chromosomal DNA. The cloned chromosomal DNA fragments were subsequently sequenced Example 4

DNA Isolation and Manipulation

Plasmid DNA was isolated from *E. coli* and *L. lactis* using the QIAprep Spin Miniprep Kit (Qiagen); for *L. lactis* however, lysozyme (15 mg/ml) was added to buffer p1 and the solution with the resuspended cells was incubated at 37° C. for 30 min before proceeding with the manufacturers protocol. Phage DNA was prepared using the Qiagen Lambda Maxi Kit (Qiagen) with the addition of proteinase K (20 mg/ml) to buffer L3 and subsequent incubation at 65° C. for 30 min before adding buffer L4. Total intracellular DNA was isolated using the method of Hill et al. (8). Restriction enzymes, T4 DNA ligase and Klenow fragment (Fermentas) were used according to the manufacturer's instructions. Electroporation of *E. coli* and *L. lactis* was performed as described previously (13). The DNA fragment corresponding to bp 1021 to 2320 (FIG. 4) in the GenBank sequence AF324839 was subcloned in the TOPO TA cloning kit prior to cloning in pCI372 and pLC5.

Example 5

DNA Sequencing and Sequence Analysis of DNA and Protein

Oligonucleotide sequences used for plasmid constructions and sequencing: For sequencing the flanking chromosomal DNA of the rescued pGhost9::ISS1 inserts a primer located in the ISS1 was used (5'-GAAGAAATGGAACGCTC-3'). Phage genome sequencing was performed with an ABI prism 3700 apparatus from the genomic platform at the research center of the Centre Hospitalier de l'Université Laval using a set of oligonucleotides previously used for sequencing of 936 phage genomes (11).

Sequence data was assembled using the Staden Pregap4 version 1.5. Sequence homology searches in databases were done using BLAST (1). Molecular weight and pI of the investigated proteins were estimated using the Protein Calculator at the website: http://www.scripps.edu/~cdputnam/protcal-c.html Example 6

A Phage Resistance Mechanism (φrm) is Found on the Chromosome of *Lactococcus lactis* subsp. *cremoris* MG1363

*L. lactis* subsp. *cremoris* MG1363 is sensitive to infection of phages from the 936 and c2 species. In this invention a transposon mutagenesis system (described in details in (10)) was used to identify a novel φrm on the chromosome of MG1363. The system (pGhost::ISS1) comprises the vector pGhost9 containing an erythromycin resistance gene ($Em^r$) and the ISS1 insertion sequence which allows for random integration of the construct into the host chromosome. Due to a thermosensitive origin of replication (plasmid is not replicating at 37° C.) it is possible to select for mutants with the construct inserted in the chromosome by growing at 37° C. in the presence of erythromycin, allowing for phenotypic expression by growing at selective conditions ON.

This selection was done for a number of independently grown cultures resulting in isolation of independent integration events. These cultures were screened for resistance to phage sk1 by selecting colonies growing on erythromycin plates in the presence of phages (MOI>1). The frequency of mutations conferring phage resistance was 100 times higher in cultures with mutants containing the pGhost::ISS1 inserts compared to the control cultures in which the phage resistance was caused by spontaneous mutations. This clearly indicates that the mutations in the phage resistant mutants containing pGhost9::ISS1 in most cases were caused by the insertion of this construct.

A number of $Em^r/φrm^+$ colonies were isolated. From four of these independently mutagenized cultures, the inserted construct was obtained along with a piece of flanking chromosomal DNA. Sequence analysis revealed insertions on the chromosome corresponding to bp 1962 (strains JH-32 and JH-46), bp 2240 (JH-48) and bp 2296 (JH-47) on the sequence available in GenBank under the accession number AF324839 (hereafter designated Lin). Bp 1021 to bp2320 therein corresponds to SEQ ID NO 6. All strains had insertions in the intergenic region between two genes (designated orf1 and trans) or in the 3' end of the trans gene (FIG. 2A). There are no genes in the same orientation immediately downstream of orf1 and since the mutagenizing constructs were all inserted in the same orientation pointing towards orf1 it was hypothesized that orf1 is encoding a φrm which is transcribed from the $Em^r$ gene promoter when pGhost::ISS1 is inserted upstream of orf1. Curing the strains for the vector (leaving a single copy of ISS1 at the insertion site) resulted in φrm⁻ phenotype supporting the hypothesis that a promoter in pGhost::ISS1 is needed for transcription of orf1 and the resulting φrm⁺ phenotype. This implies that orf1 is silent in wt MG1363 which is supported by the phage sensitive phenotype of this strain.

Example 7

Identification of orf1 as a φrm

To test if orf1 is a φrm, a fragment corresponding to bp 1021 to 2320 on the Lin sequence was cloned in the shuttle vector pCI372 (pJH6) and in the expression vector pLC5 (pJH2). These constructs were transformed in MB112 and the resulting strains (JH-53 and JH-20, respectively) were tested by cross streaking assay for resistance to phage p2. JH-53 containing pJH6 with no promoter upstream of orf1 showed no phage resistance phenotype. In comparison, JH-20 containing pJH2 with orf1 cloned downstream of a strong promoter revealed phage resistance phenotype.

To verify orf1 as being the φrm, a frameshift mutation was introduced in orf1 by filling a unique ClaI site with Klenow fragment followed by ligation and transformation of this vector (pJH3) in wt MB112. The mutated orf1 was sequenced verifying the frameshift mutation. The resulting strain JH-24 had a phage sensitive phenotype and it was therefore concluded that orf1 is encoding a φrm.

Example 8

The Isolated φrm is Effective Against Phages of the 936 and c2 Species

The three phage species 936, c2 and P335, known to be responsible for the majority of phage caused fermentation failures were tested for their sensitivity to the φrm. Four strains of the 936 species were tested against JH-20. Efficiency of plaquing (EOP) values around $10^{-4}$ were obtained for phages p2, sk1 and jj50 while phage 712 was insensitive to the φrm (Table 2). pJH2 was inserted into the host JH-22 (*L. lactis* subsp. *lactis* IL1403) which is sensitive to the 936 phages P008 and bIL170. When tested against these phages the φrm revealed EOP values around $10^{-4}$. Similar values were obtained when testing JH-20 against four phages of the c2 species (Table 2). Similar EOP values were obtained for MB112 and JH-54 when tested against the 936 and c2 phage species (data not shown), thus ruling out the possibility for the vector pLC5 being responsible for the φrm$^+$ phenotype.

TABLE 2

|  | Phage | Host strain | EOP |
|---|---|---|---|
| 936 species[a] | sk1 | JH-20 | $2.7 \pm 1.4 \times 10^{-4}$ |
|  | p2 | JH-20 | $4.8 \pm 1.8 \times 10^{-4}$ |
|  | jj50 | JH-20 | $8.3 \pm 0.5 \times 10^{-5}$ |
|  | 712 | JH-20 | $1.1 \pm 0.2$ |
|  | P008 | JH-22 | $3.8 \pm 1.5 \times 10^{-4}$ |
|  | bIL170 | JH-22 | $3.1 \pm 1.2 \times 10^{-4}$ |
| c2 species[a] | c2 | JH-20 | $5.2 \pm 0.4 \times 10^{-5}$ |
|  | bIL67 | JH-20 | $2.0 \pm 1.2 \times 10^{-4}$ |
|  | ml3 | JH-20 | $3.4 \pm 0.3 \times 10^{-4}$ |
|  | eb1 | JH-20 | $2.2 \pm 0.7 \times 10^{-4}$ |
| P335 species[b] | ul36 | JH-23 | 1.0 |
|  | KITI | JH-23 | 1.6 |
|  | Ø31 | JH-23 | 1.0 |
|  | Ø50 | JH-23 | 1.0 |
|  | Q33 | JH-23 | 0.7 |
|  | Q30 | JH-23 | 0.8 |
|  | P335 | JH-23 | 0.4 |

[a]EOP of 936 and c2 species is 1.0 on both *L. lactis* subsp. *cremoris* MG1363 (MB112) and MB112 + pLC5 (JH-54). EOP of phages P008 and bIL170 is 1.0 on *L. lactis* subsp. *lactis* IL1403
[b]EOP of P335 species is 1.0 on *L. lactis* subsp. *cremoris* (SMQ-86).

To test the φrm for efficiency against P335 phages, the φrm was inserted in a suitable host (SMQ-86) resulting in the strain JH-23. When tested against seven species of P335 phages EOP values around 1 were obtained. To rule out the possibility that modifications had taken place rendering the φrm inefficient, pJH2 was prepared from JH-23 and re-inserted into MB112 to give strain JH-26. Tests against phage p2 showed an intact φrm phenotype.

Those results showed that the φrm found on the chromosome of *L. lactis* subsp. *cremoris* MG1363 and expressed from pJH2 is effective against phages from most of the tested 936 species and all tested c2 species while no effect was seen on P335 species.

The results also showed that the φrm encoded by orf1 is efficient in both the subspecies (cremoris and lactis) of *L. lactis*.

Furthermore the results showed that EOP values did not vary whether the φrm was expressed from a promoter located in single copy on the chromosome of the host or from a strong promoter on the vector pJH2. This indicates that the efficiency of the system is not dependent on the copy number of the gene.

Example 9

Temperature Sensitivity

The efficiency of the φrm was tested against phage sk1 at 30° C. and 37° C. EOP values were in both cases around $10^{-4}$ (data not shown) indicating that the φrm is stable within this temperature range.

Example 10

Type of Phage Resistance Mechanism

A series of microbiological experiments were conducted to determine the type of φrm encoded by orf1.

An adsorption assay showed that the level of adsorption of phage p2 to cells with the expressed φrm was 95.9±10.6% compared to wt MG1363 (data not shown).

An assay was conducted where the φrm$^+$ strains JH-32, JH-46, JH-47, JH-48 and control MB112 was infected with sk1 that had been fluorescently labeled with the DNA binding dye SYBR-Gold. Following infection the fluorescently labeled phage DNA could be visualized under an epifluorescence microscope. Immediately following phage infection (MOI=10) of wt strain MB112 a fluorescent halo of adsorbed phages was seen surrounding the host cells. Less than 10 min after infection the fluorescent signal on the cell surface was decayed and instead a very bright fluorescent signal was observed in the center of the cell, thus indicating that the phage DNA had been injected into the host cell (data not shown).

The same result was obtained with the strains having the φrm$^+$ phenotype. This supports the data from the adsorption assay and also shows that the phage DNA is being injected in the φrm containing cells. These results indicate that the φrm is not an adsorption or injection blocking mechanism.

A cell survival assay showed no increased survival on cells harboring the φrm (Table 3) indicating that the host dies upon infection. The plaque size of phage p2 was smaller when assayed on φrm$^+$ cells compared to φrm$^-$ cells (Table 3). Finally, total DNA extraction from φrm$^+$ cells during a time course experiment of infection with phage p2 showed phage DNA replication which persisted in the cell throughout the experiment (FIG. 3).

TABLE 3

| Assay | MB112 (wt) | JH-20 (abiV) |
|---|---|---|
| EOP[a] | 1.0 | $4.8 \pm 1.8 \times 10^{-4}$ |
| ECOI (%)[b] | 1.0 | $0.5 \pm 0.2$ |
| Burst size (pfu/cell)[c] | $38.8 \pm 5.7$ | $11.1 \pm 5.2$ |
| fraction surviving cells[d] | $6.1 \pm 1.3 \times 10^{-5}$ | $3.1 \pm 0.3 \times 10^{-6}$ |
| phage DNA replication[e] | + | + (concatemeric) |
| plaque size (mm) | 1.5-1.7 | pinpoint - 0.7 |

[a]n = 3
[b]MOI = 0.5, n = 3
[c]MOI = 0.2, n = 3
[d]MOI = 5, n = 3
[e]MOI = 2, n = 1

All the above results confirm that the mechanism is a φrm that functions as an abortive infection mechanism. This was named AbiV.

Example 11

Sequence Analysis of the 1.3 kb DNA Fragment Containing the φrm

The DNA fragment cloned in pJH2 was sequenced (SEQ ID NO 3 and 5). The fragment consists of 1300 nucleotides.

Nucleotides 1 to 1300 correspond to nucleotides 1021 to 2320 in the Lin sequence (GenBank acc.nr: AF324839). One significant open reading frame (orf) was found encoding the polypeptide sequence shown in SEQ ID NO 1. This gene encoding the φrm was named abiV (SEQ ID NO 3) and the translated protein was named AbiV (SEQ ID NO 1). The G+C content of the gene was found to be 31.7%. This value is typical for abi mechanisms which are known to have lower G+C contents compared to the normal 37% in *L. lactis*. Searches for promoter sequences upstream of abiV (bp 1 to 430) were performed but no suitable promoter could be found in this region. This corresponds well with the hypothesis of the φrm being silent in the wt strain MB112. The translation start codon was preceded (8 bp upstream) by a ribosome binding site (5'-TGAACGGAGAG-3', underlined sequence matches consensus sequence).

Example 12

Analysis of the AbiV Protein Encoded by abiV in pJH2

Since the abiV gene is the only orf in the cloned sequence of pJH2 and a frame shift mutation in this orf causes the phage sensitive phenotype, it is concluded that the protein encoded by this gene is responsible for the φrm+ phenotype. AbiV consists of 201 amino acids and has a molecular weight of 22692 Da. The pI was estimated to be 5.37.

The protein does not contain any putative transmembrane or signal peptide motifs and it is therefore likely that the protein is cytosolic. Homology searches in databases did not reveal any homology (at amino acid or nucleotide level) to other lactococcal proteins or any proteins with known function. Likewise, no conserved domains were found in the protein.

The deduced function of AbiV is therefore new and the φrm is a novel abi mechanism.

Example 13

Effect of AbiV on Phage Life Cycle

The effects of the AbiV system was tested on the phage p2 life cycle using the phage sensitive strain MB112 and the corresponding AbiV containing strain JH-20. The following results are summarized in table 3.

The propagation of p2 on JH-20 was inhibited as seen by the EOP of ca $10^{-4}$ and the plaque size was reduced from about 1.5 mm to <1 mm. Very few of the infected cells harboring the φrm survived infection.

The ECOI on JH-20 was 0.5±0.2% indicating that only 5 out of 1000 infected cells managed to release at least one viable phage. In these successful infections the burst size was reduced by 72% (from 38.8±5.7 in MB112 to 11.1±5.2 in JH-20).

The combined negative effects of AbiV on cell survival, ECOI and burst size were the cause of the reduced plaque size and EOP of p2 on JH-20.

The replication of phage DNA was followed in a 2 h phage infection experiment of p2 on phage resistant JH-20 and phage sensitive MB112 (FIG. 3). Phage DNA was visualized by digesting the total DNA prepared from an infected cell culture with EcoRV and comparing the resulting fragments run on an agarose gel with the EcoRV restriction map of phage p2.

Ten minutes after infection replication of phage DNA was observed in both strains. In MB112 the concentration of phage DNA decreases around 40 min after infection coinciding with lysis of the sensitive host culture. On the contrary, in JH-20 the phage DNA persists throughout the experiment which was terminated after 2 h. Inspecting the EcoRV digested phage DNA fragments, two bands of 1.3 and 4 kb respectively and a 5.3 kb fragment are seen in the phage sensitive culture. The 5.3 kb fragment is spanning the cos site on the phage DNA which is the site where the replicated phage DNA is cut into identical units of complete phage genomes before packaging of the DNA into the capsids. Therefore the 1.3 and 4 kb fragments represent DNA that has been cut at the cos site. The presence of both non-resolved and resolved DNA in the phage sensitive strain is due to the continuous DNA replication throughout the phage life cycle and the simultaneous packaging of already resolved DNA into the phage capsids. In JH-20 (AbiV+) only the 5.3 kb fragment is observed which indicates that the phage DNA is not cut at the cos site in this strain.

The above results show that AbiV works after phage DNA replication and is thus categorized as a late abi mechanism. The presence of concatemeric DNA fragments (cos site not cut) further suggests that the φrm might work at a late stage for example during packaging of phage DNA into the capsids.

Example 14

Phage Genes Involved in Sensitivity to AbiV

A number of phage mutants capable of overcoming AbiV were isolated. On JH-20 AbiV-insensitive mutants of p2, sk1, jj50 and c2 were isolated and named p2.1, sk1.1, jj50.1 and c2.1, respectively. On JH-22, mutants of P008 and bIL170 were isolated and named P008.1 and bIL170.1, respectively.

The full genome of mutant p2.1 was sequenced revealing only mutations in the region around the early gene orf26 (SEQ ID NO 4). SEQ ID NO 4 encodes a polypeptide sequence denoted SEQ ID NO 2. The following polynucleotide mutations were found in phage p2.1 that escaped the AbiV-mechanism:

Two point mutations in orf26 leading to amino acid changes.
One point mutation in the intergenic region between orf26 and the upstream gene orf27
A 55 bp deletion including the startcodon and 6 downstream base pairs of orf26.

The homologues of p2 orf26 in the other phage mutants were sequenced. Nonsense mutations were observed in: orf26 (sk1.1), orf25 (jj50.1), orf33 (P008.1), e24 (bIL170.1) and a point mutation leading to an amino acid change (T to P) was seen in ell (c2.1).

These data show that AbiV-resistant phage mutants apparently fail to produce functional protein encoded by an early gene homologous to phage p2 orf26. In at least one phage mutant (p2.1), orf26 is the only gene which is mutated. Finally, phage 712 (936 species) is the only phage among the tested phages from the 936 and c2 species that does not contain an orf26 homologue. Among the wt phages of the 936 and c2 species, this phage is also the only one which is not sensitive to AbiV.

Based on the above results, it is concluded that a functional copy of phage p2 orf26 (and homologues in other phage species) is mandatory for successful φrm+ phenotype of AbiV. The gene is named sav (sensitivity to abiV) and the translated putative protein was named Sav. It is thus possible to strengthen the AbiV-mechanism by supplying the AbiV host cell with a polynucleotide sequence encoding wt Sav.

A nucleotide blastn analysis orf phage p2 orf26 revealed a high degree of sequence homology to other lactococcal phage genes: jj50 orf25 (99.7%), sk1 orf26 (99.0%), P008 orf33 (91.4%), bIL170 e24 (90.6%). Furthermore the translated p2 orf26 showed a more distant relationship (29%) with phage c2 gene e11. Despite the low degree of homology the e11 gene of phage c2 is involved in sensitivity to AbiV since a mutation in this gene helps the phage c2.1 escape AbiV. Therefore, sequences of either phage 936-like orf26 homologues (SEQ ID NO 2) or c2-like e11 homologues (SEQ ID NO 7; DNA sequence: SEQ ID NO 8, derived from accession number NC001706 disclosing the complete genome of *Lactococcus lactis* phage c2), or variants or fragments thereof are a part of the present invention.

Example 15

Analysis of the Phage p2 Gene orf26 (sav) and the Putative Protein (Sav) Encoded by this Gene The DNA fragment containing phage p2 gene orf26 and the upstream intergenic region to orf27 was sequenced on both strands. The sequenced fragment contains 499 nucleotides (SEQ ID NO 5). The sav gene consists of 384 bp (SEQ ID NO 4). Upstream of sav in a suitable (8 bp) distance is found a RBS sequence (GGATTGGGGGT, underlined sequence matches consensus sequence). No promoter sequence is found in the region between orf27 and sav. This corresponds well with the genetic structure of this region in p2 and in the closely related phage sk1. In both phages orf26 is the last gene in a putative operon consisting of orf30 to orf26 where the promoter is upstream of orf30 (4).

The sav gene is located at the end of the early transcribed region of phage p2. The putative protein Sav (SEQ ID NO 2) encoded by the gene sav consists of 128 amino acids. It has a theoretical molecular weight of 15.3 kDa and an estimated pI of 4.62. Homology searches revealed homology to a number of putative proteins in related phages of the 936 and c2 species. However, no homology was found to proteins with known function. Nor was found any conserved domains in the protein. The protein is thus new and it has not previously been associated with sensitivity to phage resistance mechanisms. SEQ ID NO 7 is present in the database under accession number NC001706 and it has not previously been associated with sensitivity to phage resistance mechanisms.

The interaction of Sav with AbiV is not known but the insensitivity to AbiV of phages with a deleted sav gene clearly indicates that sav is involved in sensitivity of the phage to the ϕrm.

Co-expression of abiV and sav in host cells will most likely enhance the efficiency of AbiV since the escaping mutant phages will have to mutate in other genes than sav. Co-expression might also broaden the range of phages against which AbiV is effective. These are so far only hypotheses but they are in the process of being tested experimentally.

Since sav has not previously been associated with any ϕrm, the AbiV ϕrm in the present invention is a new abi mechanism interacting in a so far unknown way with the sensitive phage. AbiV is therefore likely to be an efficient ϕrm capable of supplementing already isolated and used phage resistance mechanisms thus improving the field of phage resistance mechanisms.

The discovery of a phage gene involved in sensitivity to the Abi-resistance mechanism may be used for obtaining a phage resistance mechanism that is more efficient than use of the AbiV-mechanism alone. It is thus likely that the use of the wild type orf26-sequence encoding the polypeptide according to SEQ ID NO 2 and/or SEQ ID NO 7 will fully or partly prevent that the phage can escape the Abi-mechanism according to the present invention by supplying AbiV-sensitive protein (SaV) together with AbiV-protein.

The present invention thus relates to the use of polynucleotide sequences encoding both SEQ ID NO 1 and SEQ ID NO 2 and/or SEQ ID NO 7 (or a variant thereof) within a *Lactococcus* cell in order to exploit the synergy that exists in this combination. Compared to other known Abi-systems, the combination of SEQ ID NO 1 and SEQ ID NO 2 and/or SEQ ID NO 7 (or a variant thereof) in the same cell provides for a phage resistance mechanism that is extraordinarily efficient in preventing phage infections and thus preventing the emergence of AbiV-resistant phages.

Example 16

Use of Bacteria According to the Invention

The ϕrm according to the present invention can be used in connection with dairy starter cultures in existing dairy production plants to produce any fermented dairy food product.

Example 17

Construction of Expression Vector pLC5

The pGKV259 vector (18) was used as the starting molecule from which pLC5 was derived. pGKV259 was digested with PstI (located downstream from the P59 promoter) followed by gel purification. Two complementary oligonucleotides (5'-TGGATCCAAAGGAGGTCCTGCA-3' and 5'-GGACCTCCTTTGGATCCATGCA-3') were annealed together using standard procedures (16) to create a double stranded linker with PstI-compatible sticky ends. This linker also contained a unique BamHI site and a ribosome binding site (RBS: 5'-AGGAGG-3'). The linker was inserted into the PstI site of pGKV259 and the ligation mixture was transformed into *E. coli* MC1061. Transformants were selected on LB plates containing 20 µg/ml chloramphenicol. Positive clones with the linker inserted in the right direction were identified by colony PCR. Correct clones were later confirmed by sequencing. Upon introduction of the linker into pGKV259, the PstI site on the 5'-side of the linker was disrupted whereas the one on the 3'-side was conserved. Thus, a unique PstI site was created 8-bp downstream from the RBS. Cloning of an insert harboring its own ATG start codon into the PstI site of pLC5 enables efficient transcription from the P59 promoter, and translation from the introduced RBS. For this invention, however, the native RBS of AbiV and not the RBS in the vector was used for translation of the protein.

Example 18

RNA Isolation, Purification and RT-PCR Analysis of Transcription

Overnight cultures were diluted 100-fold and grown to $OD_{600}$=0.5 at 37° C. Aliquots (2 ml) were harvested by quick centrifugation (20,000 g, 30 sec) and the pellet was resuspended in a solution of 0.5 M sucrose with 60 mg/ml lysozyme. Following incubation (37° C., 15 min), the cells were pelleted and resuspended in 1 ml TRIzol Reagent (Invitrogen). Total RNA was isolated according to the manufacturer's instructions. Prior to reverse transcription (RT)-PCR, the RNA samples were treated with the DNase based TURBO DNA-free kit (Applied Biosystems).

RT-PCR was carried out using the RevertAid First Strand cDNA Synthesis kit (Fermentas) as recommended by the manufacturer. As a control, the RT-PCR procedure was carried out without reverse transcriptase to ensure that the RNA samples were free of contaminating DNA.

Example 19

Mutants of *L. lactis* subsp. *cremoris* MB112 Spontaneously Expressing AbiV

Cultures of *L. lactis* MB112 in exponential growth were mixed with the lytic phage sk1 (MOI>1) in presence of 10 mM $CaCl_2$ and incubated 10 min at room temperature before plating and incubation at 36° C. overnight. Spontaneous mutants were observed with a frequency of ca. $10^{-8}$. Forty single colonies were purified and cross-streaked against phages sk1, p2, 712 and p2.1. A bacterial mutant expressing AbiV is expected to be resistant to sk1 and p2 but sensitive to 712 and p2.1 (Table 1 and Table 2). Possible candidates were tested with EOP for resistance to phages p2, 712, p2.1. One mutant (JH-80) revealed the expected pattern of a mutant expressing AbiV with EOP values of $2\times10^{-5}$, 0.75 and 0.8, respectively.

Figure 6:
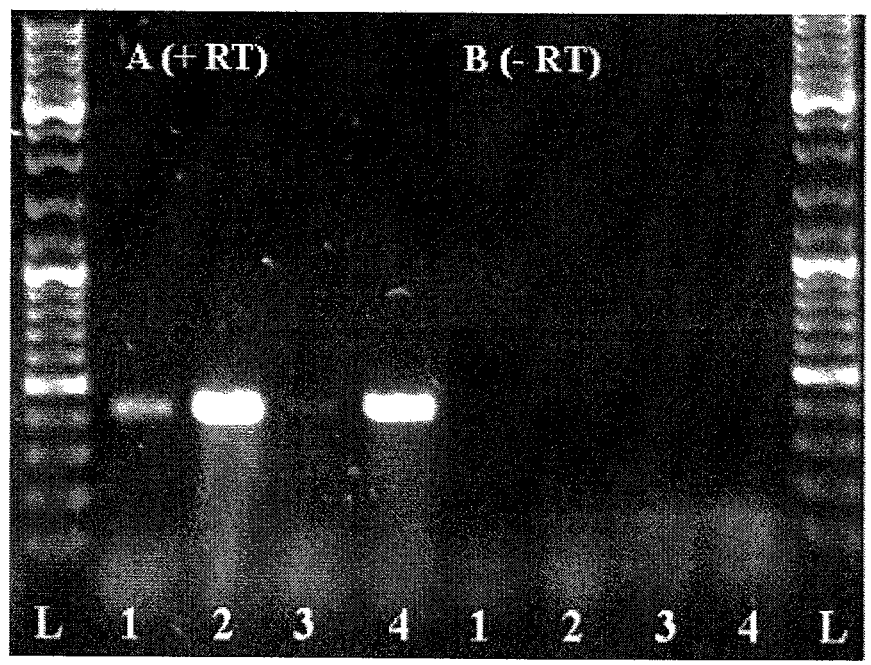
FIG. 6: Reverse transcriptase PCR carried out on isolated RNA. (A) Experiment done with reverse transcriptase enzyme. (B) Control without reverse transrciptase. Lanes 1-4 represents: JH-80 (spontaneous mutant), JH-20 (high expression of AbiV), JH-54 (wt), JH-32 (insertional mutant), respectively. L is Generuler ladder (Fermentas). The present invention will now be described in more detail in the following.

This mutant was investigated for transcription of the abiV gene using reverse transcriptase PCR (RT-PCR) (FIG. 6), as described in example 18.

These results demonstrate that it is possible to obtain mutants of *L. lactis* strains carrying abiV on the chromosome which spontaneously express AbiV. This experiment demonstrates that it is possible to obtain phage resistant bacteria expressing AbiV without using genetic modification. This is particular interesting for the dairy industry that prefers to avoid the use of genetically modified organisms (GMO).

Example 20

Conjugal Transfer of abiV

In order to improve the non-GMO alternative of the φrm invention a conjugation experiment was conducted in which the φrm was transferred from the chromosome of JH-32 (donor) to MG1614 (recipient) (Table 4). Briefly, donor and recipient were recovered from plates and mixed at high cell densities ($OD_{600}$=40). After 2 min incubation the cell mixture was plated on non-selective plates and incubated overnight in anaerobic conditions. The cells were then recovered from the plates and plated with selection for donor (erythromycin resistance), recipient (rifampicin resistance) and transconjugants (erythromycin and rifampicin resistance), respectively.

Since the erythromycin resistance gene is inserted just upstream of abiV in JH-32 the erythromycin resistance phenotype was used to select for transfer of this gene to MG1614 hoping that abiV would be transferred along with it. Rifampicin resistance was used to select for MG1614.

A number of transconjugant candidates were isolated and purified. The additional phenotypes (resistance to phage, streptomycin and fluorouracil) were used to test the isolated candidates for verification of the phage+erythromycin resistance from JH-32 to MG1614. In JH-81 the expected pattern was observed (Table 4). An EOP value of $10^{-4}$ which is similar to other EOP values obtained with AbiV (Table 2) makes it plausible that abiV was transferred and expressed in MG1614.

This experiment demonstrated that it is possible to transfer AbiV by conjugation from one bacterium to another. Conjugation is not considered as genetic modification and the method is thus suitable for the industry for transferring AbiV between bacterial strains in a non-GMO manner.

TABLE 4

Phenotype of donor (D), recipient (R) and transconjugant (T).
Selection for transconjugants was done using erythromycin and rifampicin.

| Resistance | Phage | Erythromycin | Rifampicin | Streptomycin | Fluorouracil |
|---|---|---|---|---|---|
| JH-32 (D) | yes | yes | no | no | yes |
| MG1614 (R) | no | no | yes | yes | no |
| JH-81 (T) | yes | yes | yes | yes | no |

References in Table 1
1. Bolotin, A., P. Wincker, S. Mauger, O. Jaillon, K. Malarme, J. Weissenbach, S. D. Ehrlich, and A. Sorokin. 2001. The complete genome sequence of the lactic acid bacterium *Lactococcus lactis* ssp *lactis* IL1403. Genome Research 11:731-753.
2. Emond, E., B. J. Holler, I. Boucher, P. A. Vandenbergh, E. R. Vedamuthu, J. K. Kondo, and S. Moineau. 1997. Phenotypic and genetic characterization of the bacteriophage abortive infection mechanism AbiK from *Lactococcus lactis*. Appl. Environ. Microbiol. 63:1274-1283.
3. Hayes, F., C. Daly, and G. F. Fitzgerald. 1990. Identification of the Minimal Replicon of *Lactococcus lactis* subsp. *lactis* UC317 Plasmid pCI305. Appl. Environ. Microbiol. 56:202-209.
4. Leenhouts, K., G. Buist, A. Bolhuis, B. A. ten, J. Kiel, I. Mierau, M. Dabrowska, G. Venema, and J. Kok. 1996. A general system for generating unlabelled gene replacements in bacterial chromosomes. Mol. Gen. Genet. 253: 217-224.
5. Gasson, M. J. 1983. Plasmid complements of *Streptococcus lactis* NCDO 712 and other lactic streptococci after protoplast-induced curing. J. Bacteriol. 154:1-9.
6. Maguin, E., H. Prevost, S. D. Ehrlich, and A. Gruss. 1996. Efficient insertional mutagenesis in lactococci and other gram-positive bacteria. J. Bacteriol. 178:931-935.
7. Martinussen, J. and K. Hammer. 1994. Cloning and characterization of upp, a gene encoding uracil phosphoribosyltransferase from *Lactococcus lactis*. J. Bacteriol. 176:6457-6463.

Reference List
1. Altschul, S. F., T. L. Madden, A. A. Schaffer, J. Zhang, Z. Zhang, W. Miller, and D. J. Lipman. 1997. Gapped BLAST and PSI-BLAST: a new generation of protein database search programs. Nucleic Acids Res. 25:3389-3402.
2. Behnke, D. and H. Malke. 1978. Bacteriophage interference in *Streptococcus pyogenes*. I. Characterization of prophage—host systems interfering with the virulent phage A25. Virology 85:118-128.
3. Bolotin, A., P. Wincker, S. Mauger, O. Jaillon, K. Malarme, J. Weissenbach, S. D. Ehrlich, and A. Sorokin. 2001. The complete genome sequence of the lactic acid bacterium *Lactococcus lactis* ssp *lactis* IL1403. Genome Research 11:731-753.
4. Chandry, P. S., B. E. Davidson, and A. J. Hillier. 1994. Temporal transcription map of the *Lactococcus lactis* bacteriophage sk1. Microbiology 140 (Pt 9):2251-2261.
5. Dupont, K., T. Janzen, F. K. Vogensen, J. Josephsen, and B. Stuer-Lauridsen. 2004. Identification of *Lactococcus lactis* genes required for bacteriophage adsorption. Appl. Environ. Microbiol. 70:5825-5832.
6. Emond, E., B. J. Holler, I. Boucher, P. A. Vandenbergh, E. R. Vedamuthu, J. K. Kondo, and S. Moineau. 1997. Phenotypic and genetic characterization of the bacteriophage abortive infection mechanism AbiK from *Lactococcus lactis*. Appl. Environ. Microbiol. 63:1274-1283.
7. Hayes, F., C. Daly, and G. F. Fitzgerald. 1990. Identification of the Minimal Replicon of *Lactococcus lactis* subsp. *lactis* UC317 Plasmid pCI305. Appl. Environ. Microbiol. 56:202-209.
8. Hill, C., I. J. Massey, and T. R. Klaenhammer. 1991. Rapid Method To Characterize Lactococcal Bacteriophage Genomes. Appl. Environ. Microbiol. 57:283-288.

9. Leenhouts, K., G. Buist, A. Bolhuis, B. A. ten, J. Kiel, I. Mierau, M. Dabrowska, G. Venema, and J. Kok. 1996. A general system for generating unlabelled gene replacements in bacterial chromosomes. Mol. Gen. Genet. 253:217-224.
10. Maguin, E., H. Prevost, S. D. Ehrlich, and A. Gruss. 1996. Efficient insertional mutagenesis in lactococci and other gram-positive bacteria. J. Bacteriol. 178:931-935.
11. Mahony, J., H. Deveau, G. S. Mc, M. Ventura, C. Canchaya, S. Moineau, G. F. Fitzgerald, and S. D. van. 2006. Sequence and comparative genomic analysis of lactococcal bacteriophages jj50, 712 and P008: evolutionary insights into the 936 phage species. FEMS Microbiol. Lett. 261:253-261.
12. Martinussen, J. and K. Hammer. 1994. Cloning and characterization of upp, a gene encoding uracil phosphoribosyltransferase from *Lactococcus lactis*. J. Bacteriol. 176:6457-6463.
13. Moineau, S., S. Pandian, and T. Klaenhammer. 1994. Evolution of a lytic bacteriophage via DNA acquisition from the *Lactococcus lactis* chromosome. Applied and Environmental Microbiology 60:1832-1841.
14. Moineau, S., E. Durmaz, S. Pandian, and T. R. Klaenhammer. 1993. Differentiation of Two Abortive Mechanisms by Using Monoclonal Antibodies Directed toward Lactococcal Bacteriophage Capsid Proteins. Appl. Environ. Microbiol. 59:208-212.
15. Noble, R. T. and J. A. Fuhrman. 2000. Rapid virus production and removal as measured with fluorescently labeled viruses as tracers. Appl. Environ. Microbiol. 66:3790-3797.
16. Sambrook, J. and D. W. Russell. 2001. Molecular cloning, a laboratory manual. Cold Spring Habour Laboratory Press, Cold Spring Habour, N.Y.
17. Sanders, M. E. and T. R. Klaenhammer. 1980. Restriction and Modification in Group N Streptococci: Effect of Heat on Development of Modified Lytic Bacteriophage. Appl. Environ. Microbiol. 40:500-506.
18. van der Vossen, J. M., D. van der Lelie, and G. Venema. 1987. Isolation and characterization of *Streptococcus cremoris* Wg2-specific promoters. Appl. Environ. Microbiol. 53:2452-2457.

---

The invention claimed is:

1. A starter culture composition comprising a *Lactococcus lactis* bacterium comprising a recombinant expression vector, wherein said vector encodes a polypeptide with at least 70% identity with SEQ ID NO 1 or a fragment thereof with a size of least 100 amino acids, wherein expression of said polypeptide confers at least one phage resistance mechanism to said *Lactococcus lactis* bacterium.

2. The starter culture composition according to claim 1, wherein said *Lactococcus lactis* bacterium further comprises a recombinant expression vector comprising a polynucleotide encoding a polypeptide with at least 70% identity with a sequence selected from the group consisting of: SEQ ID NO 2, a fragment of SEQ ID NO 2 that is at least 100 amino acids, SEQ ID NO 7, and a fragment of SEQ ID NO 7 that is at least 100 amino acids.

3. A method of improving phage resistance in a *Lactococcus lactis* bacterium comprising providing a *Lactococcus lactis* bacterium with an isolated polynucleotide sequence that encodes a polypeptide with at least 70% identity with SEQ ID NO 1 or a fragment thereof with a size of least 100 amino acids.

4. The method of claim 3, further comprising providing said *Lactococcus lactis* bacterium with an isolated polynucleotide that encodes a polypeptide with at least 70% identity with a sequence selected from the group consisting of SEQ ID NO 2, a fragment of SEQ ID NO 2 that is at least 100 amino acids, SEQ ID NO 7, and a fragment of SEQ ID NO 7 that is at least 100 amino acids.

5. A method of making a fermented food product comprising adding the starter culture according to claim 1 to a food product prior to fermentation of said food product, wherein said food product is selected from the group consisting of sour cream, creme fraiche, buttermilk, butter, cheese, cottage cheese, quark, cream cheese, fromage frais, yoghurt, fruit juices, fermented vegetables/fruits, and processed meat products.

6. A method of making a fermented food product comprising adding the starter culture according to claim 2 to a food product prior to fermentation of said food product, wherein said food product is selected from the group consisting of sour cream, creme fraiche, buttermilk, butter, cheese, cottage cheese, quark, cream cheese, fromage frais, yoghurt, fruit juices, fermented vegetables/fruits, and processed meat products.

7. A phage resistant *Lactococcus lactis* bacterium comprising pGhost9::ISS1 and a polynucleotide sequence encoding SEQ ID NO 1.

8. The starter culture composition according to claim 1, wherein said *Lactococcus lactis* bacterium comprises a recombinant expression vector that encodes a polypeptide with at least 70% identity with SEQ ID NO 1 and, wherein expression of said polypeptide confers at least one phage resistance mechanism to said *Lactococcus lactis* bacterium.

9. The starter culture composition according to claim 1, wherein said *Lactococcus lactis* bacterium comprises a recombinant expression vector that encodes a polypeptide with at least 80% identity with SEQ ID NO 1 and, wherein expression of said polypeptide confers at least one phage resistance mechanism to said *Lactococcus lactis* bacterium.

10. The starter culture composition according to claim 1, wherein said *Lactococcus lactis* bacterium comprises a recombinant expression vector that encodes a polypeptide with at least 90% identity with SEQ ID NO 1 and, wherein expression of said polypeptide confers at least one phage resistance mechanism to said *Lactococcus lactis* bacterium.

11. The starter culture composition according to claim 1, wherein said *Lactococcus lactis* bacterium comprises a recombinant expression vector that encodes a polypeptide having the sequence of SEQ ID NO 1 and, wherein expression of said polypeptide confers at least one phage resistance mechanism to said *Lactococcus lactis* bacterium.

12. The starter culture composition according to claim 11, wherein said *Lactococcus lactis* bacterium further comprises a recombinant expression vector comprising a polynucleotide encoding a polypeptide with at least 70% identity with a sequence selected from the group consisting of: SEQ ID NO 2, a fragment of SEQ ID NO 2 that is at least 100 amino acids, SEQ ID NO 7, and a fragment of SEQ ID NO 7 that is at least 100 amino acids.

13. The starter culture composition according to claim 8, wherein said *Lactococcus lactis* bacterium further comprises a recombinant expression vector comprising a polynucleotide encoding a polypeptide with at least 70% identity with a sequence selected from the group consisting of: SEQ ID NO 2 and SEQ ID NO 7.

14. The starter culture composition according to claim 9, wherein said *Lactococcus lactis* bacterium further comprises a recombinant expression vector comprising a polynucleotide encoding a polypeptide with at least 80% identity with a sequence selected from the group consisting of: SEQ ID NO 2 and SEQ ID NO 7.

15. The starter culture composition according to claim 10, wherein said *Lactococcus lactis* bacterium further comprises a recombinant expression vector comprising a polynucleotide encoding a polypeptide with at least 95% identity with a sequence selected from the group consisting of: SEQ ID NO 2 and SEQ ID NO 7.

16. The starter culture composition according to claim 11, wherein said *Lactococcus lactis* bacterium further comprises a recombinant expression vector comprising a polynucleotide encoding a polypeptide having a sequence selected from the group consisting of: SEQ ID NO 2 and SEQ ID NO 7.

17. The starter culture composition according to claim 11, wherein said *Lactococcus lactis* bacterium further comprises a recombinant expression vector comprising a polynucleotide encoding a polypeptide having the sequences of SEQ ID NO 2 and SEQ ID NO 7.

18. A composition comprising a *Lactococcus lactis* bacterium that comprises a recombinant expression vector, wherein said vector encodes a polypeptide with at least 70% identity with SEQ ID NO 1 or a fragment thereof with a size of least 100 amino acids, wherein expression of said polypeptide confers at least one phage resistance mechanism to said *Lactococcus lactis* bacterium.

19. The composition according to claim 18, wherein said recombinant expression vector comprises a sequence that encodes a polypeptide with at least 70% identity with SEQ ID NO 1 and, wherein expression of said polypeptide confers at least one phage resistance mechanism to said *Lactococcus lactis* bacterium.

20. The composition according to claim 18, wherein said recombinant expression vector comprises a sequence that encodes a polypeptide having the sequence of SEQ ID NO 1 and, wherein expression of said polypeptide confers at least one phage resistance mechanism to said *Lactococcus lactis* bacterium.

21. The composition according to claim 18, wherein said *Lactococcus lactis* bacterium further comprises a recombinant expression vector that comprises a polynucleotide encoding a polypeptide with at least 70% identity with a sequence selected from the group consisting of: SEQ ID NO 2, a fragment of SEQ ID NO 2 that is at least 100 amino acids, SEQ ID NO 7, and a fragment of SEQ ID NO 7 that is at least 100 amino acids.

22. The composition according to claim 21, wherein said *Lactococcus lactis* bacterium further comprises a recombinant expression vector that comprises a polynucleotide encoding a polypeptide with at least 70% identity with a sequence selected from the group consisting of: SEQ ID NO 2 and SEQ ID NO 7.

23. The composition according to claim 21, wherein said *Lactococcus lactis* bacterium further comprises a recombinant expression vector that comprises a polynucleotide encoding a polypeptide having a sequence selected from the group consisting of: SEQ ID NO 2 and SEQ ID NO 7.

24. The composition according to claim 21, wherein said *Lactococcus lactis* bacterium further comprises a recombinant expression vector that comprises a polynucleotide encoding a polypeptide having the sequences of SEQ ID NO 2 and SEQ ID NO 7.

25. The composition of claim 18, wherein said composition is a food product selected from the group consisting of sour cream, creme fraiche, buttermilk, butter, cheese, cottage cheese, quark, cream cheese, fromage frais, yoghurt, fruit juices, fermented vegetables/fruits, and processed meat products.

26. The composition of claim 21, wherein said composition is a food product selected from the group consisting of sour cream, creme fraiche, buttermilk, butter, cheese, cottage cheese, quark, cream cheese, fromage frais, yoghurt, fruit juices, fermented vegetables/fruits, and processed meat products.

* * * * *

SEQUENCE LISTING

```
<160> NUMBER OF SEQ ID NOS: 19

<210> SEQ ID NO 1
<211> LENGTH: 202
<212> TYPE: PRT
<213> ORGANISM: Lactococcus lactis
<220> FEATURE:
<221> NAME/KEY: VARIANT
<222> LOCATION: (202)..(202)
<223> OTHER INFORMATION: Xaa can be any naturally occurring amino acid

<400> SEQUENCE: 1

Met Phe Asp Lys Asp Asn Tyr Ala Leu Gly Lys Met Lys Asn Thr Leu
1               5                   10                  15

Asn Thr Lys Glu Ser Lys Phe Ser Leu Lys Ser Thr Asp Asp Leu Asn
            20                  25                  30

Lys Cys Ile Asp His Ile Ser Val Leu Ile Lys Asp Ala Tyr Leu Leu
        35                  40                  45

Tyr Thr Asn Glu Ser Phe Ala Thr Ser Thr Phe Ile Ser Ile Thr Ile
    50                  55                  60

Ile Glu Glu Val Gly Lys Thr His Ile Gly Met Phe Ile Ser Glu Asn
65                  70                  75                  80

Lys Asp Ile Lys Arg Gly Lys Asp Pro Leu Arg Asn His Lys Ser Lys
                85                  90                  95

His Ala Phe Gly Ser Leu Pro Thr Ile Lys Met Gly Gly Arg Leu Asn
            100                 105                 110

Lys Ala Ile Gly Asp Glu Met Ile Asp Lys Ile Val Glu Asp Ala Glu
        115                 120                 125

Thr Gly Glu Leu Ile Ser Ile Arg Glu Ser Ser Leu Tyr Ala Asp Ile
    130                 135                 140

Ile Asp Asp Ile Leu Glu Val Pro Ser Glu Lys Ile Ser Lys Glu Gln
145                 150                 155                 160

Ser Arg Ala Leu Leu Leu Tyr Ala Ile Glu Cys Phe Asp Asp Ser Leu
                165                 170                 175

Val Gly Tyr Thr His His Ser Phe Glu Val Ser Glu Thr Thr Asp Glu
            180                 185                 190

Leu Phe Glu Lys Leu Ala Asn Asn Lys Xaa
```

<210> SEQ ID NO 2
<211> LENGTH: 128
<212> TYPE: PRT
<213> ORGANISM: Lactococcus 1 bacteriophage

<400> SEQUENCE: 2

Met Asn Tyr Gly Thr Asn Lys His Tyr Ala Asn Glu Tyr Gly Met Glu
1               5                   10                  15

Leu Asn Glu Tyr Phe Lys His His Phe Asn Tyr Glu Glu Leu Ala Gly
            20                  25                  30

Trp Tyr Thr Met Gln Val Leu Lys Tyr Leu Val Arg Ala Gly Lys Lys
        35                  40                  45

Glu Gly Glu Ser Tyr Asp Lys Asp Arg Asn Lys Ala Leu Asp Tyr Ala
    50                  55                  60

Gly Glu Leu Ala Asn Leu Ser Asn Glu Asn Glu Leu Thr Glu Tyr Thr
65                  70                  75                  80

Thr Asp Asp Ile Met Gly Phe Ala Gln Asp Ile Ala Asp Asp Phe Lys
                85                  90                  95

Gln Trp Lys Asp Glu Arg Asn Asn Phe Lys Ser Glu Phe Thr Lys Glu
            100                 105                 110

Glu Ile Lys Ala Ile Asp Glu Arg Tyr Leu Glu Phe Ile Glu Glu Val
        115                 120                 125

<210> SEQ ID NO 3
<211> LENGTH: 603
<212> TYPE: DNA
<213> ORGANISM: Lactococcus lactis

<400> SEQUENCE: 3
atgtttgata aagacaacta tgcattagga aaaatgaaga ataccettaa taccaaagaa      60 agtaagtttt ctctaaagtc aactgatgat cttaataaat gcatcgatca tatttcagtc     120
ttaataaaag atgcatatct gctttatacg aatgaatcat ttgccacttc tacattcatt     180
tcaataacaa ttattgaaga agttggtaaa actcatatag gtatgtttat cagtgagaat     240
aaagatataa agcgtgggaa agacccttg agaaatcata atccaaaca cgcttttgga      300 tctcttccaa ctataaaaat gggaggacga cttaataagg ctattggaga tgaaatgatt     360
gataaaatcg tcgaagatgc cgaaactggt gaacttattt caatacggga gtcatctttg     420
tatgcagata ttattgatga tattcttgaa gtacctagtg aaaaaattag taagaacaa      480 agtagagcat tgctccttta tgcgatagaa tgttttgatg acagtttagt tggctataca     540
catcattcat ttgaagtatc agagacaact gatgagttgt ttgaaaagtt agcaaacaat     600
aaa                                                                   603

<210> SEQ ID NO 4
<211> LENGTH: 384
<212> TYPE: DNA
<213> ORGANISM: Lactococcus bacteriophage

<400> SEQUENCE: 4
atgaattatg gtacaaataa gcactatgcc aatgaatacg gtatggaact taacgaatac      60
tttaaacatc attttagcta tgaagagctt gcaggctggt atacaatgca ggtattaaag     120
tatctagtga gagctggcaa gaagaggggt gaaagctacg acaaagaccg taacaaggct     180
ttagactatg caggagaact tgctaactta agtaacgaga tgagcttac agaatacact      240

```
actgacgaca ttatgggctt tgcacaagat atagctgatg atttcaaaca atggaaaggc        300
gaaagaaata actttaaatc agagttcacg aaagaagaga taaaagcgat tgatgaaaga        360
tacttggaat ttattgaaga ggtc                                               384

<210> SEQ ID NO 5
<211> LENGTH: 565
<212> TYPE: DNA
<213> ORGANISM: Lactococcus bacteriophage

<400> SEQUENCE: 5
aagatacagt aaaaacttta atgatagctg taggtatagg ctttacactt atcgctatca         60
cttggatagg tataattgca acgttgctta ttacatggat tgggggtaac atctaatgaa        120
ttatggtaca ataagcact atgccaatga atacggtatg aacttaacg atactttaa         180 acatcatttt agctatgaag agcttgcagg ctggtataca atgcaggtat taaagtatct        240
agtgagagct ggcaagaaag agggtgaaag ctacgacaaa gaccgtaaca aggctttaga        300
ctatgcagga gaacttgcta acttaagtaa cgagaatgag cttacagaat cactactga        360 cgacattatg ggctttgcac aagatatagc tgatgatttc aaacaatgga aggcgaaag        420 aaataacttt aaatcagagt tcacgaaaga agagataaaa gcgattgatg aaagatactt        480
ggaatttatt gaagaggtct aaagttaatt cttgacaaat ataaagtaat ttgataatat        540
tgttttatag aaaggggatt aaaca                                              565

<210> SEQ ID NO 6
<211> LENGTH: 1300
<212> TYPE: DNA
<213> ORGANISM: Lactococcus bacteriophage

<400> SEQUENCE: 6
aaaaagagag tgggtgtatc aatttaaata taagaacttt gaagaagcct atcagagtat         60
tttctggtac atcgaagcct tttataattc aaaacgaatc catcaaagtt tagggtatct        120
tacacctaat caatttgaaa aggtaagtgc ttaaaataaa tagattaaaa ttctacgttt        180
gttactctaa aaacttgact taacgtcact tcttgagtta acttcgcata taaagaaaa        240 caaagacttt ttggatgaaa tagacaaaac ttactctaaa attgatactg tcaatactaa        300
agttagacaa actgaagtag ctgcaactac taatcaactt gcgctaacta agcaaatgt        360 acaaattcat acccttttag taattgctag taattattat caatcagtat ggatccagat        420
taaagaatga acgagagtt ttatgtttga taaagacaac tatgcattag gaaaaatgaa        480
gaataccctt aataccaaag aaagtaagtt ttctctaaag tcaactgatg atcttaataa        540
atgcatcgat catatttcag tcttaataaa agatgcatat ctgctttata cgaatgaatc        600
atttgccact tctacattca tttcaataac aattattgaa gaagttggta aaactcatat        660
aggtatgttt atcagtgaga ataaagatat aaagcgtggg aaagacccct tgagaaatca        720
taaatccaaa cacgcttttg gatctcttcc aactataaaa atgggaggac gacttaataa        780
ggctattgga gatgaaatga ttgataaaat cgtcgaagat gccgaaactg gtgaacttat        840
ttcaatacgg gagtcatctt gtatgcaga tattattgat gatattcttg aagtacctag        900
tgaaaaaatt agtaaagaac aaagtagagc attgctccctt tatgcgatag aatgttttga        960
tgacagttta gttggctata cacatcattc attgaagta tcagagacaa ctgatgagtt       1020
gtttgaaaag ttagcaaaca ataaaatagt aaatcttgag tttgattttg ctgaatattc       1080
tgcatttatc gggcggaatg atgccctag actttgcaac agaacctcga ttttaattcg       1140
```

```
ttcagaatag gttatactag acaaaagatc ggctcctaaa aatgggtttg tgataaacac    1200
cattttaaag gaagctggtc ttttttgtcc aaacactggt cagacaattt tggggcctat    1260
gatatttggt gttgatagat aaaattcatc aacactattc                          1300
```

```
<210> SEQ ID NO 7
<211> LENGTH: 123
<212> TYPE: PRT
<213> ORGANISM: Lactococcus bacteriophage c2
<220> FEATURE:
<221> NAME/KEY: VARIANT
<222> LOCATION: (123)..(123)
<223> OTHER INFORMATION: Xaa can be any naturally occurring amino acid

<400> SEQUENCE: 7
```

Met Ala Gln Asp Tyr Tyr Ala Asn Lys Tyr Gly Ile Gln Leu Glu Glu
1               5                   10                  15

Phe Leu Ile Trp Gly Ser Glu Trp Asp Leu Lys Phe Trp Lys Tyr Asn
            20                  25                  30

Phe Thr Thr Gly Gln Gly Phe Ala Leu Thr Asn Ala Leu Lys Tyr Thr
        35                  40                  45

Val Arg Ala Gly Lys Lys Pro Asp Glu Pro Tyr Glu Lys Asp Met Gly
50                  55                  60

Lys Tyr Asn Asp Tyr Ile Asp Met Ala Val Lys Met Gly Phe Glu Arg
65                  70                  75                  80

Ser Glu Ala Glu Asp Trp Val Ala Leu Gln Lys Ser Ile Phe Glu Glu
                85                  90                  95

Phe Lys Gly Lys Lys Ala Glu Ile Glu Glu Leu Glu Lys Arg Lys Glu
            100                 105                 110

Met Lys Glu Asn Asp Glu Ile Arg Arg Leu Xaa
        115                 120

```
<210> SEQ ID NO 8
<211> LENGTH: 366
<212> TYPE: DNA
<213> ORGANISM: Lactococcus bacteriophage c2

<400> SEQUENCE: 8
atggctcaag attattatgc aaataagtac ggtattcaat agaagagtt cctgatttgg     60 ggttctgaat gggacttaaa attttggaag tataacttta caactggtca aggttttgca   120
ctaactaacg ctttaaagta cactgtaagg gcagggaaaa agccagatga accgtatgaa   180
aaagatatgg gcaaatataa cgactacatc gacatggctg ttaaaatggg ctttgaacgg   240
tctgaagcag aagactgggt agcacttcaa aaatcaatat ttgaggagtt taaaggaaaa   300
aaagcagaaa ttgaagaact tgaaaaaaga aaggaaatga agaaaatga tgaaattcgt   360 cgcctt                                                              366
```

```
<210> SEQ ID NO 9
<211> LENGTH: 11
<212> TYPE: DNA
<213> ORGANISM: Lactococcus bacteriophage

<400> SEQUENCE: 9
agaaaggagg t                                                         11
```

```
<210> SEQ ID NO 10
<211> LENGTH: 11
<212> TYPE: DNA
<213> ORGANISM: Lactococcus bacteriophage
```

```
<400> SEQUENCE: 10
agaaaggagg t                                                          11

<210> SEQ ID NO 11
<211> LENGTH: 17
<212> TYPE: DNA
<213> ORGANISM: Lactococcus bacteriophage

<400> SEQUENCE: 11
gaagaaatgg aacgctc                                                    17

<210> SEQ ID NO 12
<211> LENGTH: 11
<212> TYPE: DNA
<213> ORGANISM: Lactococcus bacteriophage

<400> SEQUENCE: 12
tgaacggaga g                                                          11

<210> SEQ ID NO 13
<211> LENGTH: 11
<212> TYPE: DNA
<213> ORGANISM: Lactococcus bacteriophage

<400> SEQUENCE: 13
ggattggggg t                                                          11

<210> SEQ ID NO 14
<211> LENGTH: 22
<212> TYPE: DNA
<213> ORGANISM: Lactococcus bacteriophage

<400> SEQUENCE: 14
tggatccaaa ggaggtcctg ca                                              22

<210> SEQ ID NO 15
<211> LENGTH: 22
<212> TYPE: DNA
<213> ORGANISM: Lactococcus bacteriophage

<400> SEQUENCE: 15
ggacctcctt tggatccatg ca                                              22

<210> SEQ ID NO 16
<211> LENGTH: 6
<212> TYPE: DNA
<213> ORGANISM: Lactococcus bacteriophage

<400> SEQUENCE: 16 aggagg                                                                 6

<210> SEQ ID NO 17
<211> LENGTH: 1300
<212> TYPE: DNA
<213> ORGANISM: Lactococcus lactis

<400> SEQUENCE: 17
aaaaagagag tgggtgtatc aatttaaata taagaacttt gaagaagcct atcagagtat     60
tttctggtac atcgaagcct tttataattc aaaacgaatc catcaaagtt tagggtatct    120
tacacctaat caatttgaaa aggtaagtgc ttaaaataaa tagattaaaa ttctacgttt    180
gttactctaa aaacttgact taacgtcact tcttgagtta acttcgcata ataaagaaaa    240
```

```
caaagacttt ttggatgaaa tagacaaaac ttactctaaa attgatactg tcaatactaa      300
agttagacaa actgaagtag ctgcaactac taatcaactt gcgctaacta aagcaaatgt      360
acaaattcat acccttttag taattgctag taattattat caatcagtat ggatccagat      420
taaagaatga acggagagtt ttatgtttga taaagacaac tatgcattag gaaaaatgaa      480
gaatacccct aataccaaag aaagtaagtt ttctctaaag tcaactgatg atcttaataa      540
atgcatcgat catatttcag tcttaataaa agatgcatat ctgctttata cgaatgaatc      600
atttgccact tctacattca tttcaataac aattattgaa gaagttggta aaactcatat      660
aggtatgttt atcagtgaga ataaagatat aaagcgtggg aaagacccct tgagaaatca      720
taaatccaaa cacgcttttg gatctcttcc aactataaaa atgggaggac gacttaataa      780
ggctattgga gatgaaatga ttgataaaat cgtcgaagat gccgaaactg gtgaacttat      840
ttcaatacgg gagtcatctt tgtatgcaga tattattgat gatattcttg aagtacctag      900
tgaaaaaatt agtaaagaac aaagtagagc attgctccct tatgcgatag aatgttttga      960
tgacagttta gttggctata cacatcattc atttgaagta tcagagacaa ctgatgagtt     1020
gtttgaaaag ttagcaaaca ataaatagtt aaatcttgag tttgattttg ctgaatattc     1080
tgcatttatc gggcggaatg atgcccttag actttgcaac agaacctcga ttttaattcg     1140
ttcagaatag gttatactag acaaaagatc ggctcctaaa aatgggtttg tgataaacac     1200 catttttaaag gaagctggtc ttttttgtcc aaacactggt cagacaattt tggggcctat     1260
gatatttggt gttgatagat aaaattcatc aacactattc                           1300

<210> SEQ ID NO 18
<211> LENGTH: 499
<212> TYPE: DNA
<213> ORGANISM: Lactococcus bacteriophage

<400> SEQUENCE: 18
aagatacagt aaaaacttta atgatagctg taggtatagg ctttacactt atcgctatca       60
cttggatagg tataattgca acgttgctta ttacatggat tgggggtaac atctaatgaa      120
ttatggtaca aataagcact atgccaatga atacggtatg gaacttaacg aatactttaa      180
acatcatttt agctatgaag agcttgcagg ctggtataca atgcaggtat taaagtatct      240
agtgagagct ggcaagaaag agggtgaaag ctacgacaaa gaccgtaaca aggctttaga      300
ctatgcagga gaacttgcta acttaagtaa cgagaatgag cttacagaat acactactga      360
cgacattatg ggctttgcac aagatatagc tgatgatttc aaacaatgga aaggcgaaag      420
aaataacttt aaatcagagt tcacgaaaga agagataaaa gcgattgatg aaagatactt      480
ggaatttatt gaagaggtc                                                   499

<210> SEQ ID NO 19
<211> LENGTH: 11
<212> TYPE: DNA
<213> ORGANISM: Lactococcus

<400> SEQUENCE: 19
agaaaggagg t                                                            11
```